United States Patent [19]

Nakajima et al.

[11] Patent Number: 5,447,158
[45] Date of Patent: Sep. 5, 1995

[54] ULTRASONIC IMAGING METHOD AND SYSTEM CAPABLE OF DISPLAYING B-MODE IMAGE AND COLOR FLOW MAPPING IMAGE OVER WIDE FIELD

[75] Inventors: Hirotaka Nakajima; Noriaki Yoshikawa; Masahiko Yano, all of Tochigiken, Japan

[73] Assignee: Kabushiki Kaisha Toshiba, Kawasaki, Japan

[21] Appl. No.: 77,356

[22] Filed: Jun. 16, 1993

[30] Foreign Application Priority Data

Jun. 16, 1992 [JP] Japan .................................. 4-156333

[51] Int. Cl.$^6$ ............................................. A61B 8/06
[52] U.S. Cl. ............................................. 128/661.09
[58] Field of Search ...................... 128/660.04, 660.05, 128/661.01, 661.09, 661.1; 73/625–626

[56] References Cited

U.S. PATENT DOCUMENTS

| | | | |
|---|---|---|---|
| 4,915,115 | 4/1990 | Sasaki et al. | 128/660.05 |
| 4,972,838 | 11/1990 | Yamazaki | 128/660.05 X |
| 5,014,710 | 5/1991 | Maslak et al. | 128/660.05 |
| 5,105,813 | 4/1992 | Shikato | 128/660.07 |
| 5,148,810 | 9/1992 | Maslak et al. | 128/661.01 |
| 5,165,413 | 11/1992 | Maslak et al. | 128/660.05 |
| 5,235,986 | 8/1993 | Maslak et al. | 128/661.01 |
| 5,261,408 | 11/1993 | Maslak et al. | 128/661.01 |

Primary Examiner—Francis Jaworski
Attorney, Agent, or Firm—Oblon, Spivak, McClelland, Maier, & Neustadt

[57] ABSTRACT

In ultrasonic imaging method/system, a deep interior portion of a biological body under medical examination can be scanned by blood-flow image scanning beams with a wide view field. The ultrasonic imaging system is arranged by a probe device having a probe plane for transmitting ultrasonic pulses to an interior portion of a biological body under medical examination, and for receiving ultrasonic echoes reflected from the interior portion of the biological body; a B-mode image scanning unit coupled to the probe means, for scanning the interior portion of the biological body by the ultrasonic pulses in a fan-shaped form as fan-shaped B-mode image scanning beams; a B-mode image producing unit for producing B-mode image data of the scanned interior portion from B-mode imaging echoes derived from the probe device, while scanning the interior portion by the fan-shaped B-mode image scanning beams; a blood-flow image scanning unit for scanning the interior portion by transmitting thereto the ultrasonic pulses as blood-flow image scanning beams from the probe plane at a predetermined inclined angle with respect to a normal line direction of the probe plane; a blood-flow image producing unit for producing blood-flow image data of the scanned interior portion from blood-flow imaging echoes derived from the probe means, while scanning the interior portion by the inclined blood-flow image scanning beams; and a dual-mode displaying unit for displaying both of a B-mode image of the scanned interior portion the a blood-flow image thereof in a dual mode by superimposing the blood-flow image data on the B-mode image data.

13 Claims, 21 Drawing Sheets

----- CFM SCANNING LINES
——— B-MODE SCANNING LINES

B1,B2,----Bn : B-MODE SCANNING LINES

F1, F2, ---Fn : B-MODE SCANNING LINES
F1', F2'---Fn': CFM-MODE SCANNING LINES

ULTRASONIC IMAGING METHOD AND SYSTEM CAPABLE OF DISPLAYING B-MODE IMAGE AND COLOR FLOW MAPPING IMAGE OVER WIDE FIELD

BACKGROUND OF THE INVENTION

1. Field of the Invention

The present invention generally relates to ultrasonic imaging method and system with a dual display mode. More specifically, the present invention is directed to ultrasonic imaging method and system capable of displaying both of a B-mode ultrasonic image of a biological body under medical examination and a color Doppler image (or color flow mapping image) thereof over a wide field even in a deep interior portion by freely setting a beam steering direction.

2. Description of the Prior Art

Various types of ultrasonic imaging systems with a dual display mode, capable of displaying both of a B-mode image and a CFM image on a single display screen in a superimpose mode have been developed. The conventional ultrasonic imaging systems employ, for instance, a linear ultrasonic probe to perform either the linear scanning mode, or the sector scanning mode. In the linear scanning mode, a tissue section within a biological body under medical examination is scanned by ultrasonic beams positioned parallel to each other to produce a B-mode image and also a color blood-flow image (or CFM image) of the scanned interior tissue. In the sector scanning mode, the ultrasonic beam scanning is carried out for the interior tissue from a predetermined point in a radial form to produce these images.

Typically, the Doppler method has been widely utilized to acquire such a color blood-flow image, or a color flow mapping (CFM) image. The basic blood-flow measurement by Doppler method will now be summarized with reference to FIG. 1. In FIG. 1, an ultrasonic probe 1 is employed to project ultrasonic beams 2 therefrom to an interior portion of a biological body 3 under medical examination having blood vessels 4. The frequency of the ultrasonic beams 2 is selected to be "$f_o$". When the ultrasonic beams 2 having the frequency of "$f_o$" collide with red blood cells 5 which are moving at a velocity of "v", echoes having a frequency of "$f_o'$" are reflected from these red blood cells 5 due to the Doppler effect. That is, assuming now that the transmission frequency of the ultrasonic beam 2 is "$f_o$"; the reception frequency of the echo is "$f_o'$", and an incident angle between the ultrasonic beam 2 and the blood flow direction is "$\theta$", the velocity of the blood flow "v" is calculated based on an equation (1):

$$fd = f_o' - f_o \frac{2vf_o \cos\theta}{c}, \quad (1)$$

where symbol "fd" indicates a shifted frequency, and symbol "c" denotes the sound velocity.

Accordingly, a frequency shift is proportional to cosine of the angle intersecting between the ultrasonic beam 2 and the blood flow direction as shown in the equation (1). When the ultrasonic beam 2 is positioned in parallel to the blood flow, the frequency shift becomes maximum, so that the frequency shift can be measured at high precision. When the ultrasonic beam 2 intersects with the blood flow at a right angle (90°), the frequency shift becomes zero, so that this Doppler frequency-shift measurement can not be performed. Generally speaking, since blood vessels 4 are located parallel with a surface of the biological body 3, when the ultrasonic beams used for the color flow mapping are transmitted toward the surface of the biological body 3 at the right angle, these ultrasonic beams intersect with the blood flow direction at 90°. As a result, the blood flow velocity cannot be measured (namely, cosine 90°=0).

As the possible conventional methods for avoiding that the CFM measuring beam 2 intersects with the blood-flow direction at a right angle, there are two typical ultrasonic beam scanning methods. A first conventional beam scanning method is shown in FIG. 2. In FIG. 2, B-mode imaging ultrasonic beams 6B are transmitted from a probe surface 1S of the probe 1 at a right angle, whereas CFM imaging ultrasonic beams 6C are transmitted from this probe surface 1S at a certain inclined angle. In this linear scanning method, a rectangular-shaped B-mode image is displayed with a CFM image of a portion of this rectangular shape in a superimpose mode. FIG. 3 represents a second conventional beam scanning method in which both of B-mode imaging ultrasonic beams 8B and CFM imaging ultrasonic beams 8C are transmitted at a certain inclined angle. As a result, a color blood flow (CFM) image having a shape of parallelogram is displayed.

These B-mode/CFM-mode beam scanning methods are known from, for instance, U.S. Pat. No. 5,014,710 issued on May 14, 1991 to Maslak et al., entitled "STEERED LINEAR COLOR DOPPLER IMAGING", and Japanese Laid-open (KOKAI DISCLOSURE) Patent No. 62-227335 opened on Oct. 6, 1987.

On the other hand, in order to easily specify a position of a CFM image on a monitor screen, this CFM (color blood-flow) image is superimposed on a B-mode image in the conventional ultrasonic imaging systems. Accordingly, in the above-explained first linear scanning method shown in FIG. 2, only a color blood-flow image of a portion 7 where the B-mode imaging beams 6B transmitted from the probe surface 1S at a right angle intersects with the CFM-mode imaging beam 6C transmitted at a certain inclined angle can be displayed on a monitor screen. As easily understood from such a limited CFM image portion 7, since the area 7 of the CFM image is especially narrowed at the deep portion, it is difficult to diagnose either a kidney, or a liver located in a deep portion of a biological body, while observing such a narrow CFM image.

To improve difficulties of the narrow CFM image portion 7, the second conventional linear scanning method as shown in FIG. 3 has been proposed in which both of the B-mode imaging beam 8B and the CFM-mode imaging beam 8C are transmitted from the probe 1 at the same inclined angle with respect to the probe surface 1S, i.e., a surface of a biological body. Accordingly, a color blood-flow image having a shape of a parallelogram is displayed whose area is wider than the above-described CFM image area 7 of the first ultrasonic imaging method.

However, this second ultrasonic imaging method has the problems. Since only the color blood-flow image located oblique from the probe 1 is displayed, it is rather difficult to grasp where a curing portion (CFM-scanned portion) is actually located within the biological body. In particular, when a deep portion of the biological body is diagnosed, a great positional difference may be induced, which will deteriorate correct positioning precision for such a curing portion in the ultrasonic diagnose.

SUMMARY OF THE INVENTION

The present invention has been made in an attempt to solve the above-described problems of the conventional B-mode/CFM-mode imaging ultrasonic scanning methods, and therefore, has an object to provide an ultrasonic imaging system capable of displaying both of a B-mode image and a CFM-mode image of a wide viewing field from a surface of a biological body to a deep portion thereof.

To achieve the above-described object, an ultrasonic imaging system, according to one aspect of the present invention, comprises:

probe means (10:10A:102) having a probe plane (11S:30S) for transmitting ultrasonic pulses (2) to an interior portion of a biological body (3) under medical examination, and for receiving ultrasonic echoes reflected from the interior portion of the biological body (3);

B-mode image scanning means (25:17:16) coupled to the probe means, for scanning said interior portion of the biological body (3) by said ultrasonic pulses (2) in a fan-shaped form as fan-shaped B-mode image scanning beams (A1:B1:F1);

B-mode image producing means (15:19:20:23) for producing B-mode image data of said scanned interior portion from B-mode imaging echoes derived from said probe means, while scanning said interior portion by said fan-shaped B-mode image scanning beams (A1:B1:F1);

blood-flow image scanning means (25:17:16) for scanning said interior portion, while transmitting thereto said ultrasonic pulses (2) as blood-flow image scanning beams (A1':B1':F1') from said probe plane (11S:30S) at a preselected inclined angle ($\theta k$) with respect to a normal line direction of said probe plane (11S:30S);

blood-flow image producing means (15:19:21) for producing blood-flow image data of said scanned interior portion from blood-flow imaging echoes derived from said probe means, while scanning said interior portion by said inclined blood-flow image scanning beams (A1':B1':F1'); and dual-mode displaying means (24) for displaying both of a B-mode image of said scanned interior portion and a blood-flow image thereof in a dual mode by superimposing said blood-flow image data on said B-mode image data.

Furthermore, according to another aspect of the present invention, an ultrasonic imaging system comprises:

probe means (10:10A:102) having a probe plane (11S:30S) for transmitting ultrasonic pulses (2) to an interior portion of a biological body (3) under medical examination, and for receiving ultrasonic echoes reflected from the interior portion of the biological body (3);

B-mode image scanning means (25:17:16) coupled to the probe means, for scanning said interior portion of the biological body (3) by said ultrasonic pulses (2) in a fan-shaped form as fan-shaped B-mode image scanning beams (A1:B1:F1);

B-mode image producing means (15:19:20:23) for producing B-mode image data of said scanned interior portion from B-mode imaging echoes derived from said probe means, while scanning said interior portion by said fan-shaped B-mode image scanning beams (A1:B1:F1);

blood-flow image scanning means (25:17:16) for scanning said interior portion, while transmitting thereto said ultrasonic pulses (2) as blood-flow image scanning beams (A1':B1':F1') from said probe plane (11S:30S) at a preselected inclined angle ($\theta k$) with respect to a normal line direction of said probe plane (11S:30S);

blood-flow image producing means (15:19:21) for producing blood-flow image data of said scanned interior portion from blood-flow imaging echoes derived from said probe means, while scanning said interior portion by said inclined blood-flow image scanning beams (A1':B1':F1');

angle correcting means (22) for correcting a color indication of a blood-flow direction of blood, said color indication being varied in accordance with an incident angle of said blood-flow image scanning beams (C1':D1':F1') with respect to said blood-flow direction of the blood within a blood vessel (5), even when said blood is flown along the same direction; and dual-mode displaying means (24) for displaying both of a B-mode image of said scanned interior portion and a blood-flow image thereof in a dual mode by superimposing said blood-flow image data on said B-mode image data.

In accordance with another aspect of the present invention, an ultrasonic imaging method comprises the steps of:

transmitting ultrasonic pulses from a probe plane (11S:30S) of an ultrasonic probe (10:10A:102) to an interior portion of a biological body (3) under medical examination;

receiving ultrasonic echoes reflected from the interior portion of the biological body (3);

scanning said interior portion of the biological body (3) by said ultrasonic pulses (2) in a fan-shaped form as fan-shaped B-mode image scanning beams (A1:B1:F1);

producing B-mode image data of said scanned interior portion from B-mode imaging echoes derived from said probe, while scanning said interior portion by said fan-shaped B-mode image scanning beams (A1:B1:F1);

scanning said interior portion, while transmitting thereto said ultrasonics pulses (2) as blood-flow image scanning beams (A1':B1':F1') from said probe plane (11S:30S) at a preselected inclined angle ($\theta k$) with respect to a normal line direction of said probe plane (11S:30S);

producing blood-flow image data of said scanned interior portion from blood-flow imaging echoes derived from said probe, while scanning said interior portion by said inclined blood-flow image scanning beams (A1':B1':F1'); and displaying both of a B-mode image of said scanned interior portion and a blood-flow image thereof in a dual mode by superimposing said blood-flow image data on said B-mode image data.

According to a further aspect of the present invention, an ultrasonic imaging method comprises the steps of:

transmitting ultrasonic pulses (2) from a probe plane (11S:30S) of an ultrasonic probe (10:10A:102) to an interior portion of a biological body (3) under medical examination;

receiving ultrasonic echoes reflected from the interior portion of the biological body (3);

scanning said interior portion of the biological body (3) by said ultrasonic pulses (2) in a fan-shaped form as fan-shaped B-mode image scanning beams (A1:B1:F1);

producing B-mode image data of said scanned interior portion from B-mode imaging echoes derived from said probe, while scanning said interior portion by said fan-shaped B-mode image scanning beams (A1:B1:F1);

scanning said interior portion, while transmitting thereto said ultrasonic pulses (2) as blood-flow image scanning beams (A1':B1':F1') from said probe plane (11S:30S) at a preselected inclined angle ($\theta k$) with respect to a normal line direction of said probe plane (11S:30S);

producing blood-flow image data of said scanned interior portion from blood-flow imaging echoes derived from said probe, while scanning said interior portion by said inclined blood-flow image scanning beams (A1':B1':F1');

correcting a color indication of a blood-flow direction of blood, said color indication being varied in accordance with an incident angle of said blood-flow image scanning beams (C1':D1':F1') with respect to said blood-flow direction of the blood within a blood vessel (5), even when said blood is flown along the same direction; and displaying both of a B-mode image of said scanned interior portion and a blood-flow image thereof in a dual mode by superimposing said blood-flow image data on said B-mode image data.

In accordance with the present invention, the steering angle of the ultrasonic beams is freely settable, so that various scanning modes can be realized, for instance, a so-called "fan-shaped linear scanning" mode (will be described later), and a trapezoid scanning mode.

BRIEF DESCRIPTION OF THE DRAWINGS

For a better understanding of the present invention, reference is made of the following detailed description in conjunction with the accompanying drawings, in which.

DETAILED DESCRIPTION OF THE PREFERRED EMBODIMENTS

OVERALL CIRCUIT ARRANGEMENT OF FIRST ULTRASONIC IMAGING SYSTEM

Figure 4:
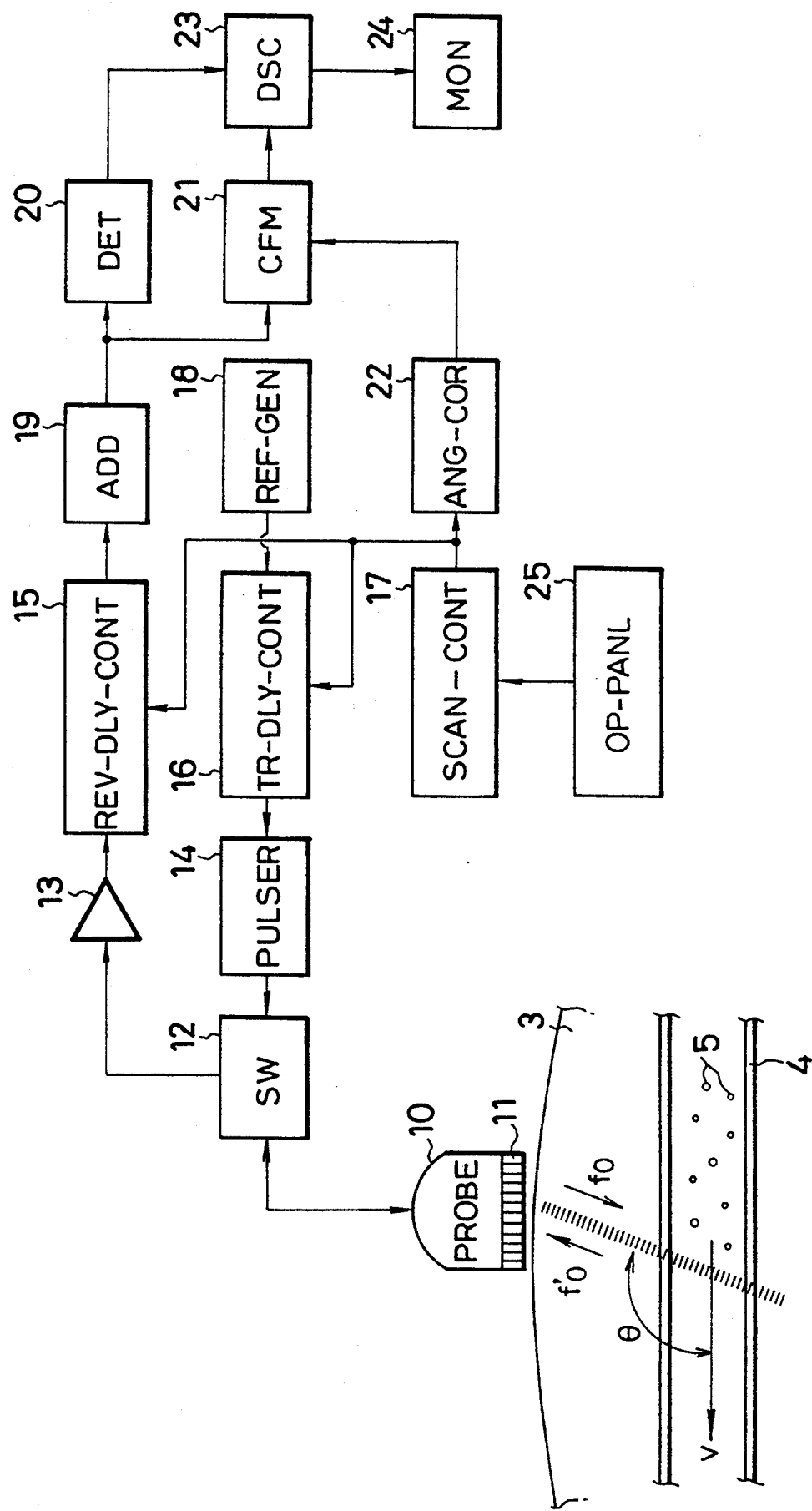
FIG. 4 is a schematic block diagram of an overall circuit of an ultrasonic imaging system according to a first preferred embodiment of the present invention.

FIG. 4 is a schematic block diagram of an overall circuit arrangement of an ultrasonic imaging system according to a first preferred embodiment of the present invention.

In this circuit arrangement, an ultrasonic imaging probe 10 includes a transducer array constructed of "N" pieces ("N" being an integer greater than 1) of transducer elements 11. A reference signal generator 18 generates a reference signal having a frequency of "$f_o$" which will be supplied to a transmission delay control circuit 16. A scanning controller 17 is employed to calculate an actual scanning direction of an ultrasonic scanning beam (see FIG. 5) based upon the selected scanning method and scanning direction, which are designated by an operator on an operation panel 25. Then, the calculated actual scanning direction data is supplied to a reception delay control circuit 15, the transmission delay control circuit 16, and an angle correction circuit 22. The transmission delay control circuit 16 subdivides the reference signal supplied from the reference signal generator 18 into signals for N channels. The delay times determined based upon the actual scanning directions calculated in the scanning controller 17 are applied to these subdivided reference signals for N channels in this transmission delay control circuit 16. The resultant delayed reference signals are supplied to a pulser circuit 14. The pulser circuit 14 converts these delayed reference signals for N channels into pulse signals for N channels, which will then be supplied to the above-described ultrasonic probe 10 via a selecting switch 12. These pulse signals are used to energize the corresponding transducer elements 11, thereby producing "N" pieces of ultrasonic beams (see FIG. 5). These ultrasonic beams are transmitted from the transducer elements 11 of the ultrasonic probe 10 to an interior of the biological body 3. That is, these ultrasonic beams are used to scan inside of the biological body 3 along the scanning directions calculated by the scanning controller 17 (will be described in detail).

The transmitted ultrasonic beams are reflected within the biological body 3, and then the reflected beams are returned as echoes to the transducer elements 11 of the ultrasonic probe 10, so that echo signals for N channels are produced from the transducer elements 11. The echo signals produced by the ultrasonic probe 10 are supplied via the selecting switch. 12 to a preamplifier 13. In this preamplifier 13, the echo signals for N channels are amplified and thereafter sent to the above-described reception delay control circuit 15. In this reception delay control circuit 15, predetermined delay times calculated based upon the scanning directions obtained in the scanning controller 17 are applied to the echo signals for N channels amplified in the preamplifier 13 so as to correct the temporal shifts contained in the echo signals for N channels. Then, the temporal-corrected echo signals are supplied to an adder 19. In this adder 19, the respective echo signals are summed with each other, which will then be supplied to a detecting circuit 20 and a CFM (color flow mapping) circuit 21. The detecting circuit 20 detects the summed echo signal to produce B-mode image information. On the other hand, the CFM circuit 21 produces color blood-flow (CFM) information based on the summed echo signal derived from the adder 19. In a DSC (digital scan converter) circuit 23, the B-mode image data derived from the detecting circuit 20 is synthesized with the CFM image data described from the CFM circuit 21, and the synthesized image data is converted into a standard television signal which will then be supplied to a TV monitor 24. As a result, a B-mode image of the biological body 3 is displayed with a CFM image of a designated portion within the B-mode image in a superimpose mode.

In this first ultrasonic imaging system, an angle correcting circuit 12 is employed. This angle correcting circuit 12 previously stores correction data used to correct shifts of color blood flow information caused by incident angles of the CFM-mode scanning beams, and produces correction signals for correcting shifts of the color blood flow information based on the scanning direction data obtained in the scanning controller 7 (will be described in detail). Furthermore, the operation panel 25 is employed to select the scanning modes and to designate the display position of the color blood flow information with respect to the B-mode image.

DEFINITION OF "FAN-SHAPED LINEAR SCANNING MODE"

Before describing an overall operation of the first ultrasonic imaging system, a so-called "fan-shaped linear" scanning mode realized in this first ultrasonic imaging system will now be explained with reference to FIG. 5.

Figure 5:
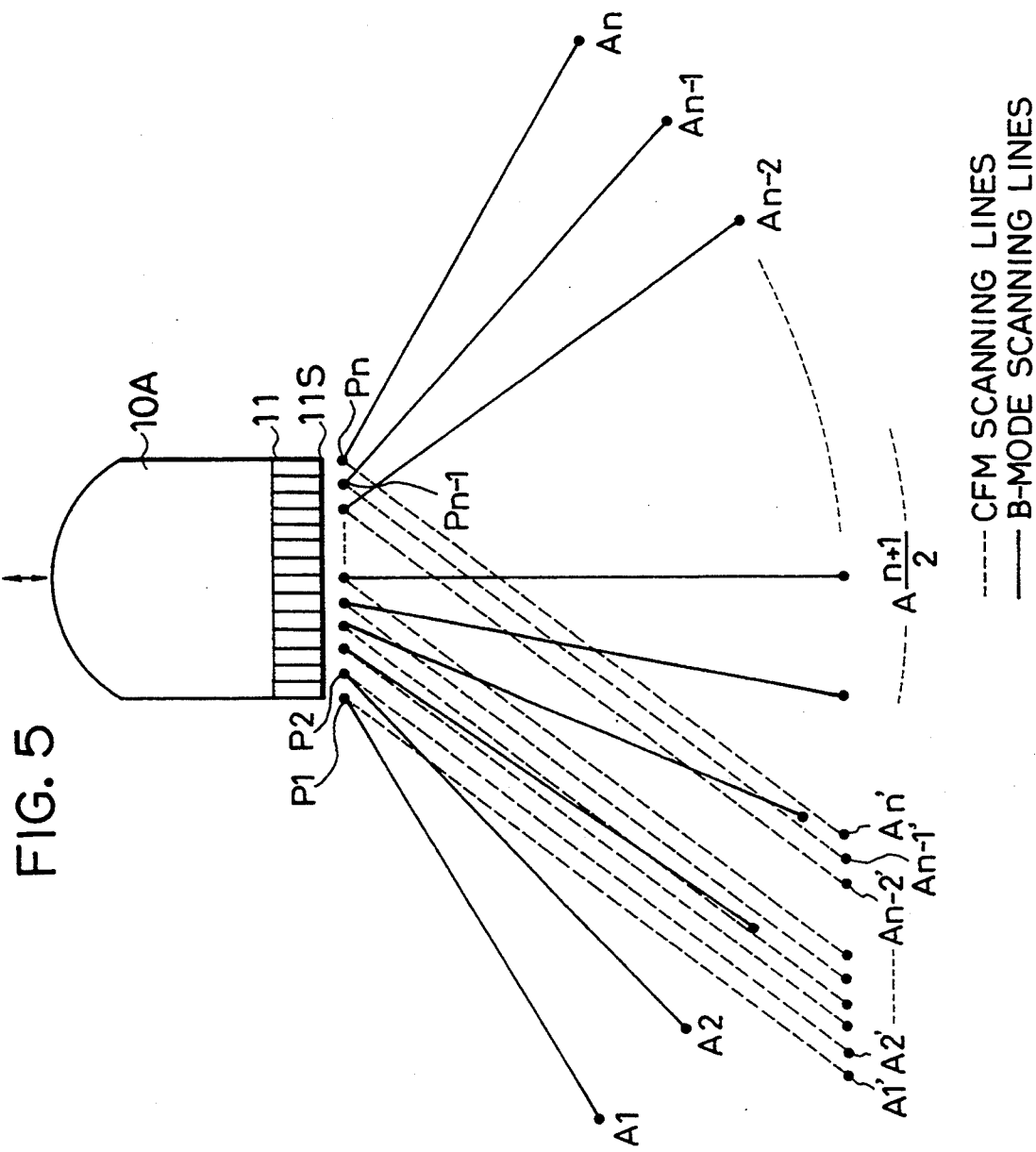
FIG. 5 schematically shows both of the B-mode scanning lines and the CFM-mode scanning lines of the fan-shaped linear scanning in the first ultrasonic imaging system.

FIG. 5 schematically shows a linear probe 10A in which "N" pieces of ultrasonic transducer elements 11 are arranged in a linear form. This linear probe 10A is used as the probe 10 of the first ultrasonic imaging system shown in FIG. 4.

In FIG. 5, symbols A1, A2, - - -, An indicate scanning lines used for a B-mode image, and symbols A1', A2', - - -, An' denote scanning lines used for a CFM-mode image. The scanning lines A1, A2, - - -, An ("n" being an integer) constitute such a linear scanning operation that these scanning lines are positioned in the non-parallel form with each other. Then, a width of a scanning range of this fan-shaped linear scanning mode adjacent a surface of the biological body 3 (see FIG. 4) is substantially equal to a width of the probe plane 11S of this linear probe 10A, and another width of this fan-shaped linear scanning range is considerably wider than the width of this probe plane 11S in a deep portion of the biological body.

B-MODE SCANNING LINES OF FIRST ULTRASONIC IMAGING SYSTEM

The B-mode scanning lines A1, A2, - - -, An transmitted from the linear probe 10A will now be explained with reference to FIG. 6 more in detail. In this enlarged view of the scanning lines, only odd-numbered scanning lines A1, A3, A5, - - -, An-1 are drawn for the sake of easy illustration.

Figure 6:
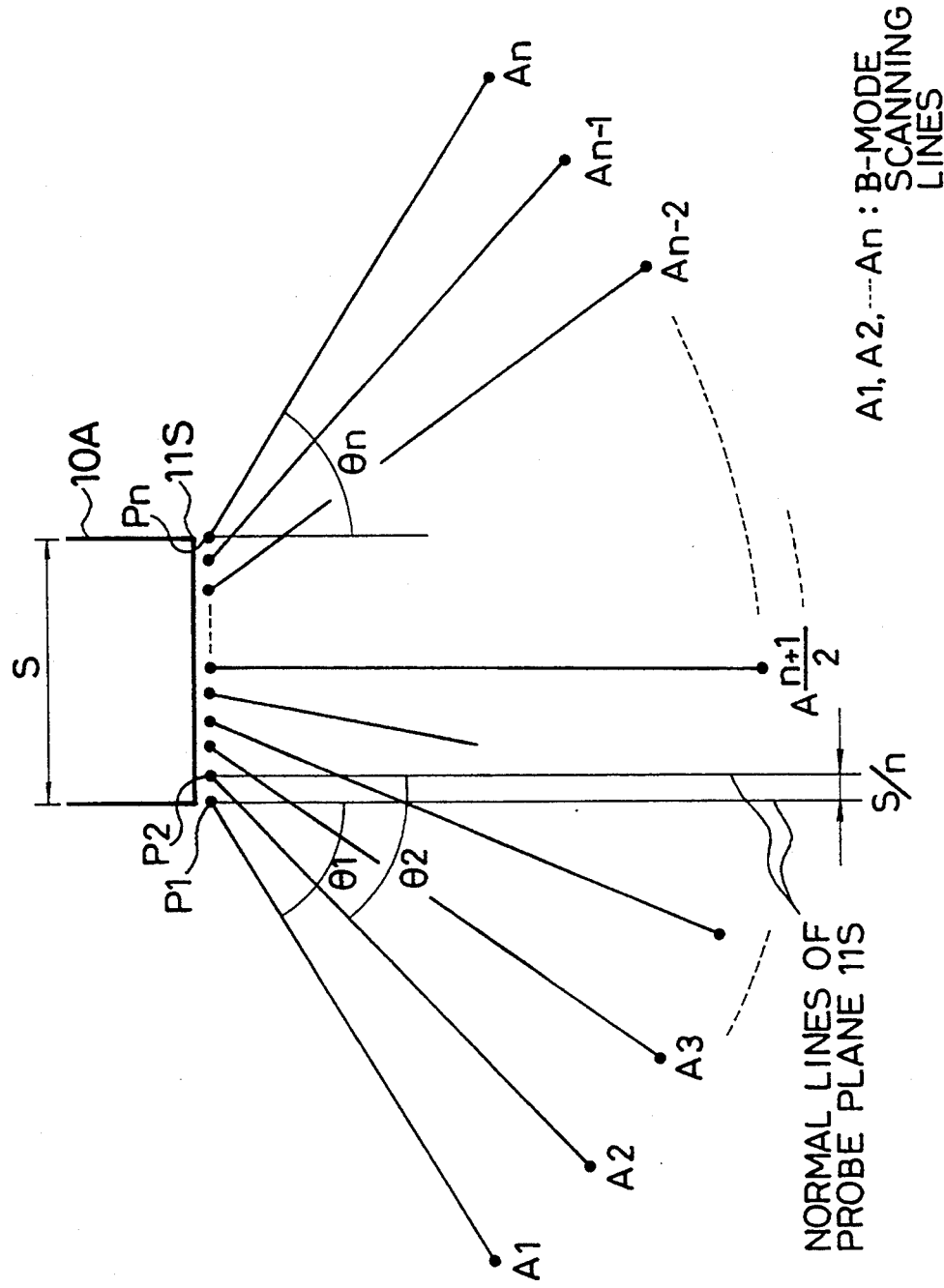
FIG. 6 is an enlarged illustration of the B-mode scanning lines employed in the first ultrasonic imaging system.

In FIG. 6, symbol "S" shows a width of the probe plane 11S of this linear probe 10A in the horizontal direction. Symbols P1, P2, - - -, Pn denote starting points of scanning operations for the scanning lines A1, A2, - - -, An, and the scanning lines A1', A2', - - -, An'. An interval of the respective scan-starting points shows S/n. Symbols $\theta 1, \theta 2, - - -, \theta n$ indicate angles defined by the respective scanning lines A1, A2, - - -, An and the respective normal lines of the probe plane 11S.

In the first ultrasonic imaging system shown in FIG. 4, the fan-shaped linear scanning operation is performed in a symmetrical form with respect to one scanning line A (n+1)/2 along the horizontal direction. To perform such a symmetrical scanning operation, a value of an angle $\theta k$ (k<n) is defined by the following equation (2):

$$\theta k = \theta 1 - (k-1) \cdot \frac{2 \cdot \theta 1}{n-1} \qquad (2)$$

Furthermore, a scan-starting point "Pk" is calculated by the below-mentioned equation (3):

$$Pk = (k-1) \cdot \frac{S}{n}, \qquad (3)$$

where P1 is assumed as 0.

B-MODE SCANNING OPERATION OF FIRST ULTRASONIC IMAGING SYSTEM

The B-mode scanning operation of the first ultrasonic imaging system shown in FIGS. 4 and 6 will now be described, which is operated under the so-called "fan-shaped linear scanning mode".

In the first ultrasonic imaging system of FIG. 4, the scanning controller 17 calculates data about the scanning-start points and the scanning directions for the respective B-mode scanning lines. A pair of scanning-start point data and scanning direction data with respect to each of the B-mode scanning lines "A1" to "An" are successively supplied from this scanning controller 17 to the reception delay control circuit 15 and the transmission delay control circuit 16. As a result, the biological body 3 is sequentially scanned along the B-mode scanning lines A1 to An (see FIG. 6) in the fan-shaped linear scanning mode.

The echo signals obtained from the interior portions of the biological body 3 along these B-mode scanning lines A1 to An are detected by the detector 20, and the detected echo signals are supplied to the DSC circuit 23. In this DSC circuit 23, the fan-shaped B-mode image is obtained from the detected echo signals and then stored in a memory device (will be discussed later) employed in the DSC circuit 13.

It should be noted as the major feature of the first ultrasonic imaging system that since the beam steering angle "$\theta k$" may be varied by operating the operation panel 25, the display area (region) of the B-mode image at the deep portion of the biological body 3 may be made narrow, or wide.

CFM-MODE SCANNING LINES OF FIRST ULTRASONIC IMAGING SYSTEM

The CFM-mode scanning lines A1', A2', - - -, An' are shown as an enlarged form in FIG. 7, which will now be explained more in detail.

Symbols P1', P2', - - -, Pn' indicate scanning-start points of these CFM-mode scanning lines A1', A2', - - -, An'. An interval between the successive scanning-start points P1', P2', - - -, Pn' is defined as S/n. An angle $\theta'$ denotes an angle between each of these CFM scanning lines A1', A2', - - -, An' and the normal line of the plane 11S (will be referred to a "beam steering angle" hereinafter).

It should be noted that in this first ultrasonic imaging system, the beam steering angles $\theta'$ for the respective CFM-mode scanning lines A1', A2', - - -, An' and the normal line of the probe plane 11S are equal to each other. Accordingly, these CFM-mode scanning lines A1', A2', - - -, An' are positioned in parallel to each other, as represented in FIG. 7.

CFM-MODE SCANNING OPERATION OF FIRST ULTRASONIC IMAGING SYSTEM

The CFM-mode scanning operation of the first ultrasonic imaging system shown in FIGS. 4 and 7 will now be described, which is operated under the so-called "fan-shaped linear scanning mode".

In the first ultrasonic imaging system of FIG. 4, the scanning controller 17 calculates data about the scanning-start points and the scanning directions for the respective B-mode scanning lines. It should be understood that since the scanning start points P1, P2, - - -, Pn of the CFM-mode scanning lines A1', A2', - - -, An' are identical to those of the B-mode scanning lines A1, A2, - - -, An (see FIG. 6), no further calculation of the above-described equation (3) is required, and since the CFM scanning lines A1', A2', - - -, An' are positioned in parallel to each other, once a certain angle $\theta'$ is determined, only a simple calculation of the above-described equation (2) is performed. A pair of scanning-start point data and scanning direction data with regard to each of the CFM-mode scanning lines A1' to An' are sequentially supplied from this scanning controller 17 to the reception delay control circuit 15 and the transmission delay control circuit 16. As a result, the biological body 3 is sequentially scanned along the CFM-mode scanning lines A1' to An' (see FIG. 7).

The echo signals obtained from the interior portions of the biological body 3 along these CFM-mode scanning lines A1' to An' are supplied from the adder circuit 19 to the CFM circuit 21. The CFM circuit 21 obtains a color blood-flow image based on these echo signals, in which a difference in the blood-flow velocities is indicated by different colors. Thereafter, the color blood-flow image data is supplied to the DSC circuit 23, so that this color blood-flow image is superimposed on the above-described B-mode image. As a consequence, both of the fan-shaped B-mode image and the color blood-flow image are displayed on the monitor screen 24 in such a manner that this color blood-flow image is superimposed on a portion of this fan-shaped B-mode image.

It should be noted that since the beam steering angle $\theta'$ of the CFM-mode scanning line may be similarly varied by operating the operation panel 25, the display position of the color blood-flow image may be shifted along the horizontal direction by changing this beam steering angle $\theta'$.

INTERNAL CIRCUIT OF SCANNING CONTROLLER 17

Figure 8:
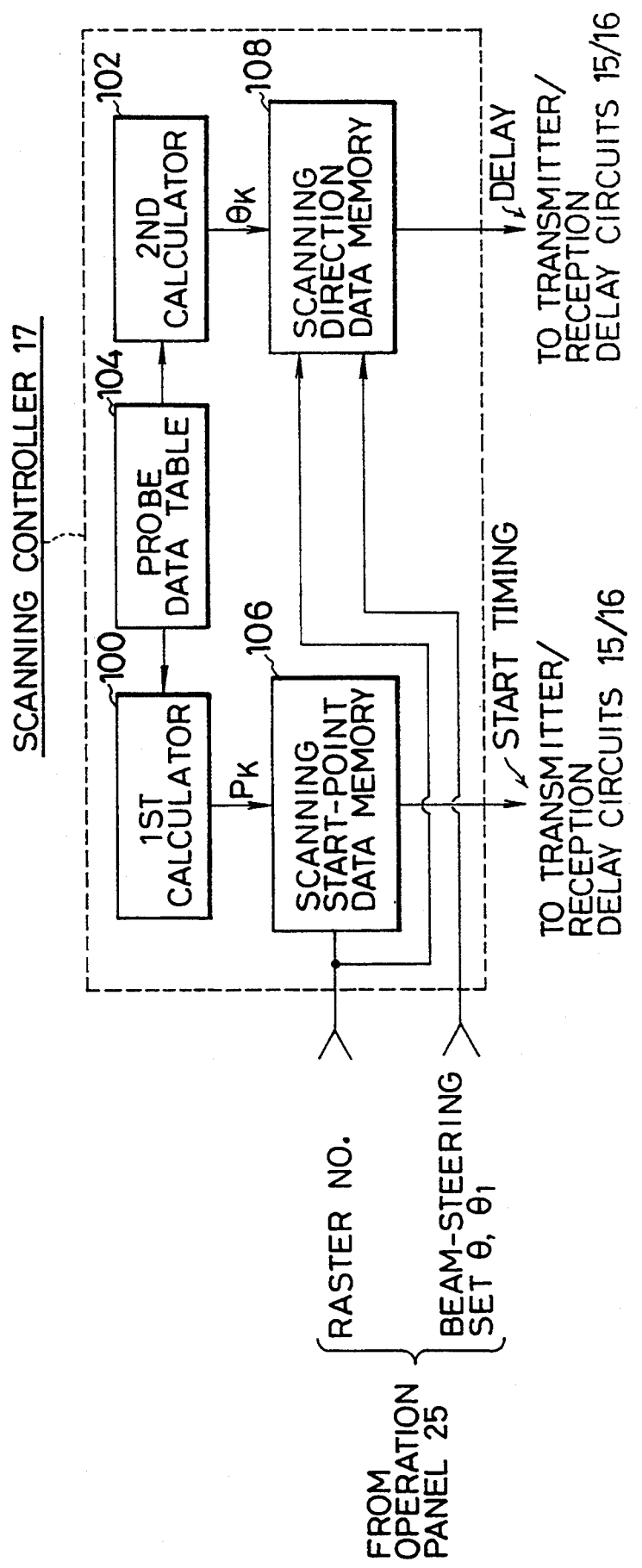
FIG. 8 is an internal circuit arrangement of the scanning controller 17 employed in the first ultrasonic imaging system.

FIG. 8 is an internal circuit arrangement of the above-described scanning controller 17 which constitutes one of major features of the first ultrasonic imaging system shown in FIG. 4. As described above, this scanning controller 17 mainly performs calculations of desired scanning directions/scanning start-points for the respective B-mode/CFM-mode scanning lines A1, A2, A3, - - -, An in order to freely set the steering angles of the respective ultrasonic beams emitted from the probe 10A. In other words, since the scanning controller 17 can freely control the scanning operation for the scanning beams A1, A2, - - -, An, the desired scanning mode such as a so-called "fan-shaped linear scanning" mode can be realized, while observing a deep interior portion of scanned biological body 3.

In FIG. 8, the scanning controller 17 employs a first calculator 100 and a second calculator 102. Furthermore, a probe data table 104, a scanning start-point data memory 106, and a scanning direction data memory 108 are provided. The scanning start-point data memory 106 receives the raster number data derived from the operation panel 25 and stores the scanning start-point data calculated in the first calculator 100. On the other hand, the scanning direction data memory 108 receives the raster number data and the beam steering set data, which are supplied from the operation panel 25, and also stores the scanning direction data (i.e., delay data) calculated in the second calculator 102.

Referring now to FIG. 8, a detailed operation of this scanning controller 17 will now be described.

As an initial operation in the first ultrasonic imaging system of FIG. 4, an operator manipulates the operation panel 25 to set such initial condition that the linear scanning probe 10A as shown in FIG. 5 is mounted and the beam steering angle "$\theta k$" ($1 \leq k \leq n$) is set so as to realize the "fan-shaped linear scanning" at a desired interior region within the biological body 3 with regard to the depth direction (vertical direction as viewed in FIG. 5) and the scanning direction (horizontal direction as viewed in FIG. 5).

There are two types of beam steering angle setting operations, namely for B-mode image and CFM-mode image (will be described later).

Furthermore, the operator designates through the operation panel 25 the raster number. For instance, as to the frame alternate scanning operation, the scanning line numbers A1, A2, - - -, An for the B-mode image are designated. and the scanning line numbers A1', A2', - - -, An' for the CFM-mode image are designated. In contrast thereto, as to the raster alternate scanning operation, the scanning line numbers A1, A1', A2, A2', - -

—, An and An′ are designated for both of the B-mode image and the CFM-mode image.

In should be noted that the "frame alternate scanning" is designated in this first ultrasonic imaging system.

In the scanning controller 17, the first calculator 100 calculates the scanning start point "P1" for the first scanning line A1 in accordance with the above-explained formula (3) by utilizing the probe data table 104. Then, the calculated scanning start-point data (P1) is stored in the scanning start-point data memory 106. Subsequently, this calculation/storage operation is continued for the remaining scanning lines A2, A3, - - - , An.

On the other hand, the second calculator 102 calculates the scanning direction "$\theta 1$" for the first scanning line A1 in accordance with the previously explained formula (2) by utilizing probe data table 104. Then, the calculated scanning direction data ($\theta 1$), or delay data is stored in the scanning direction data memory 108. Subsequently, this calculation/storage operation is continued for the remaining scanning lines A2, A3, - - - , An.

As previously described, in the first ultrasonic imaging system of FIG. 4, the scanning controller 17 calculates data about the scanning-start points and the scanning directions for the respective B-mode scanning lines. A pair of scanning-start point data and scanning direction data with respect to each of the B-mode scanning lines "A1" to "An", are successively supplied from the scanning start-point data memory 106 and the scanning direction data memory 108 of this scanning controller 17 to the reception delay control circuit 15 and the transmission delay control circuit 16. As a result, the biological body 3 is sequentially scanned along the B-mode scanning lines A1 to An (see FIG. 6) in the fan-shaped linear scanning mode.

The echo signals obtained from the interior portions of the biological body 3 along these B-mode scanning lines A1 to An, are detected by the detector 20, and the detected echo signals are supplied to the DSC circuit 23. In this DSC circuit 23, the fan-shaped B-mode image is obtained from the detected echo signals and then stored in a memory device (will be discussed later) employed in the DSC circuit 13.

As to the CFM-mode image scanning operation, since a similar operation is carried out, no further description is made in the following description.

Figure 9:
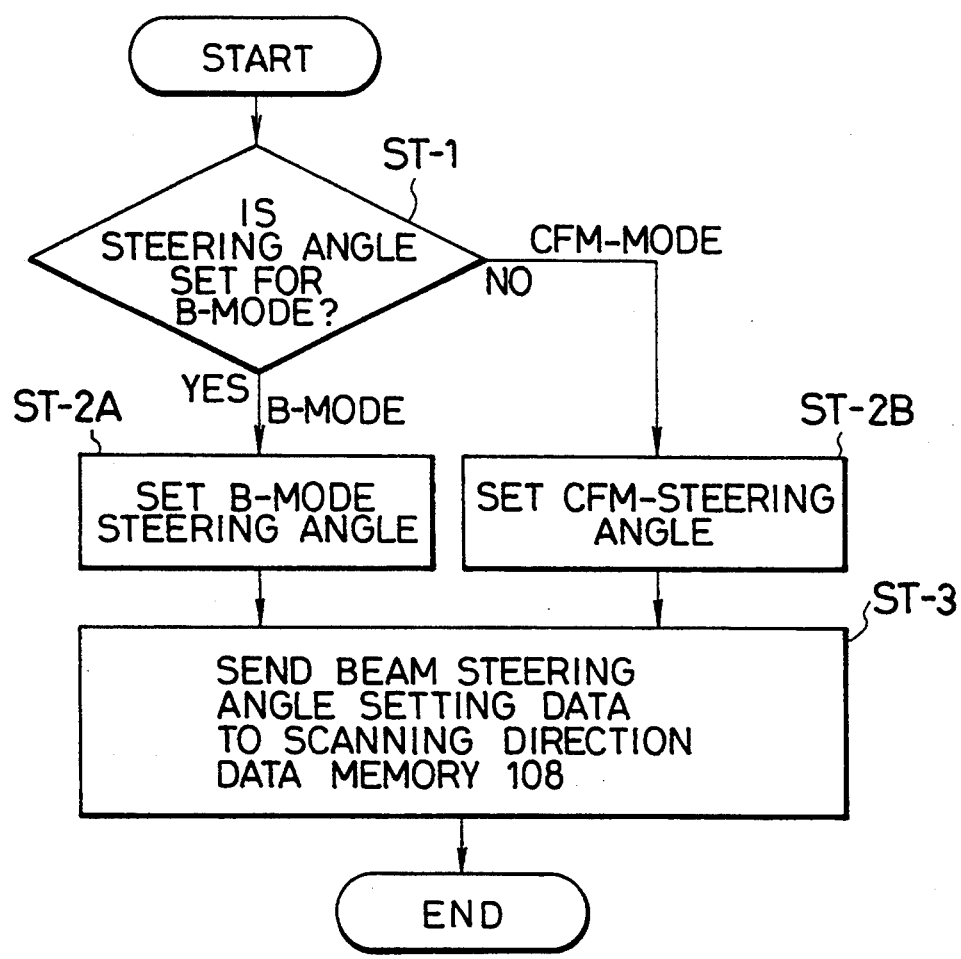
FIG. 9 is a flow chart for explained an operation of the scanning controller 17.

Referring now to a flow chart of FIG. 9, an overall operation with regard to the scanning control for the B-mode and the CFM-mode operations will be summarized.

At a first step ST-1 of this flow chart, a check is done as to whether the beam steering angle is set to the B-mode image, or the CFM-mode image. If the B-mode image is selected, then the beam steering angle setting operation for the B-mode image is carried out at a step ST-2A. To the contrary, if no B-mode image is selected, then the beam steering angle setting operation for the CFM-mode image is performed at a step ST-2B.

Thereafter, both of the beam steering angle setting data for the B-mode image and the CFM-mode image are supplied to the scanning direction data memory 108 employed in the scanning controller 17.

Figure 10:
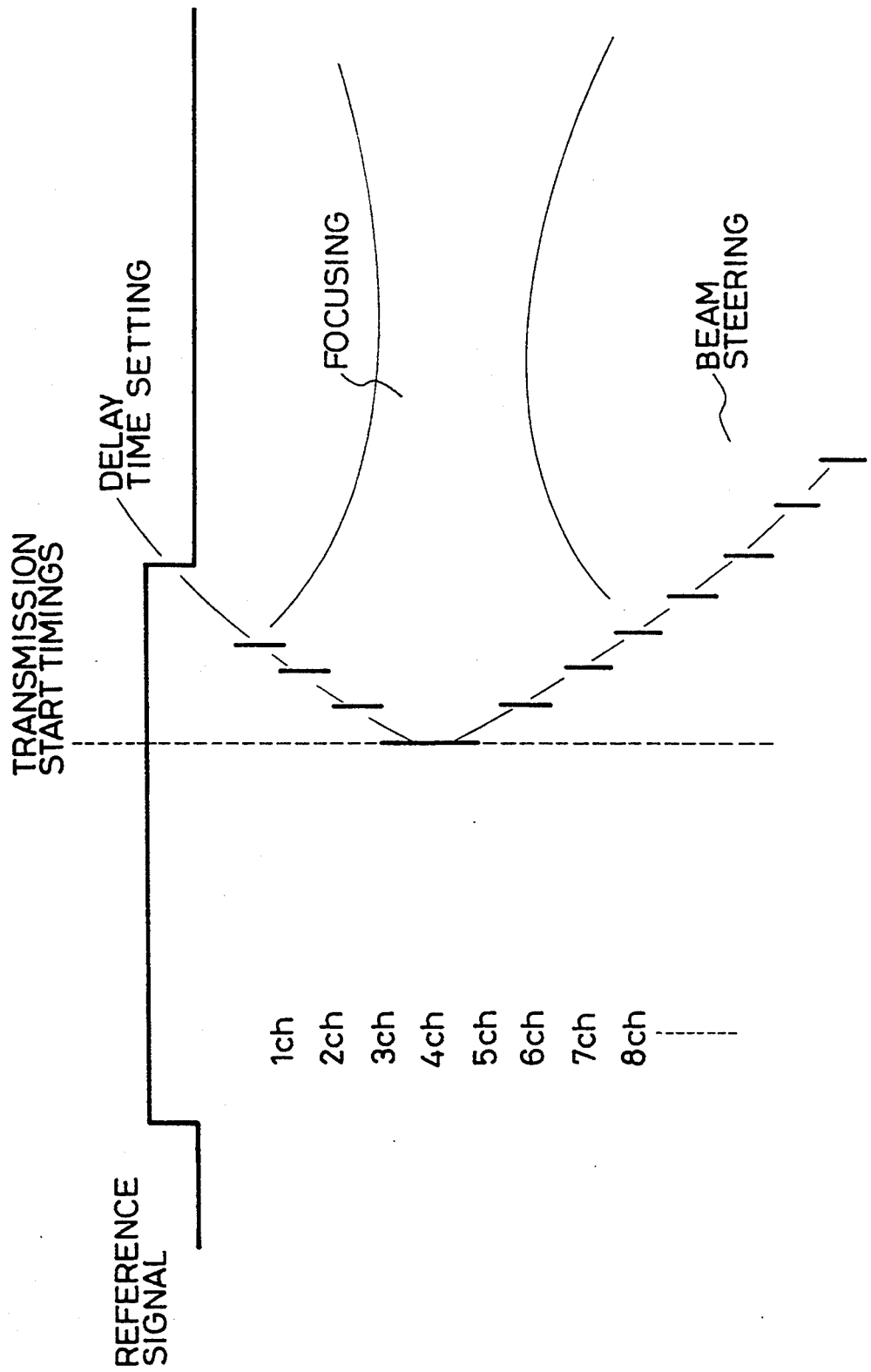
FIG. 10 schematically illustrates the focusing and beam steering operation performed in the first ultrasonic imaging system.

FIG. 10 illustratively explains how to perform a focusing operation of the ultrasonic beams and also to execute a beam steering operation in the fist ultrasonic imaging system shown in FIG. 4.

As previously described in detail, the first ultrasonic imaging system shown in FIGS. 4–10 owns the following advantages. Since the B-mode image is shaped as a "fan", the color blood-flow image with such a wide range can be displayed on the TV monitor 24. Moreover, since the displayed range of this B-mode image is also wide, it can be readily grasped which interior portion of the biological body 3 is being represented on the monitor screen. As a consequence, it is no longer require to move the ultrasonic probe 10A many times along the surface of the biological body 3 in order to specify an actual position of a curing portion thereof, which may improve ultrasonic diagnose.

SECOND ULTRASONIC IMAGING SYSTEM EMPLOYING CONVEX PROBE

Figure 11:
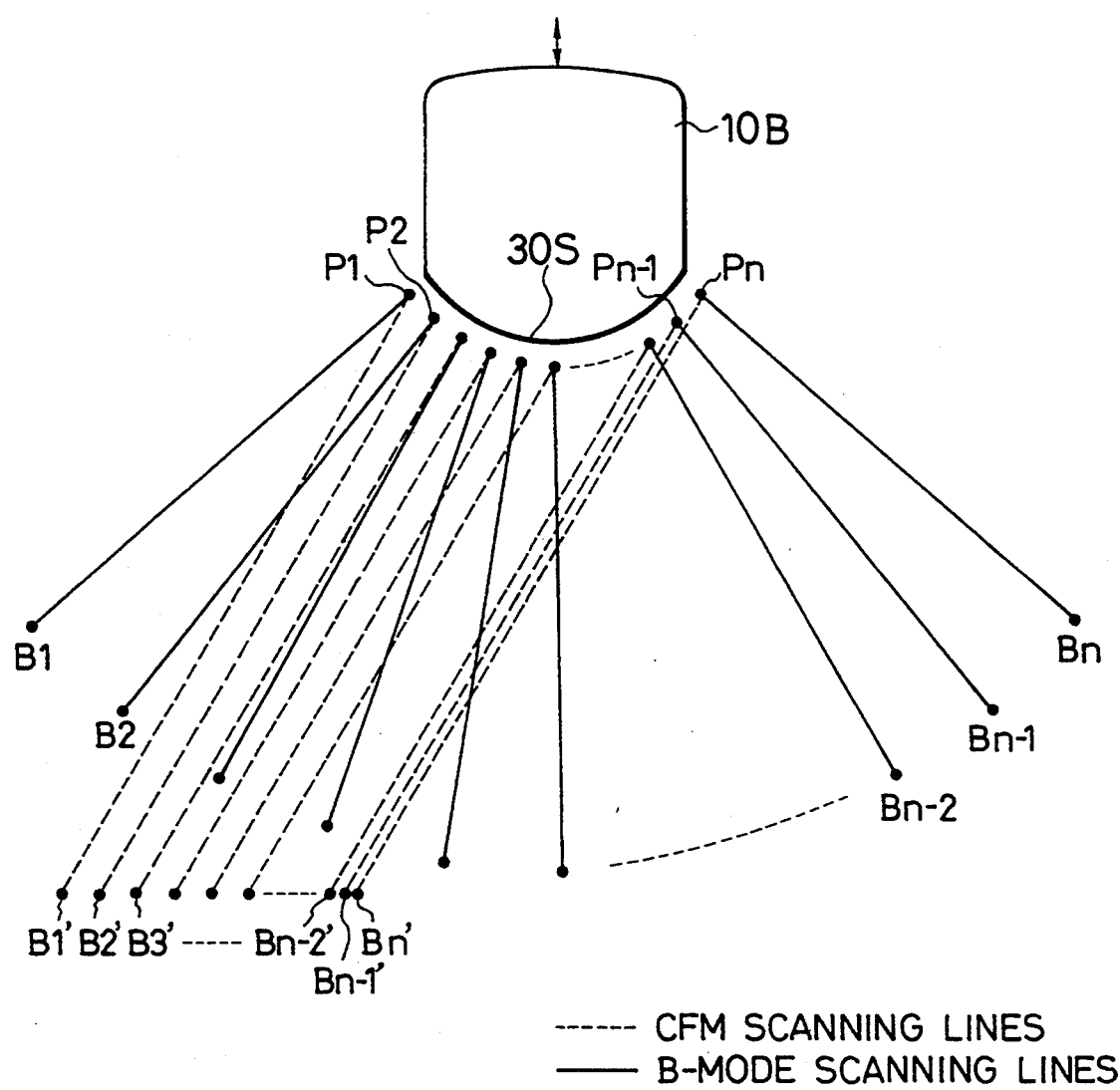
FIG. 11 schematically shows the fan-shaped B-mode linear scanning and the parallel CFM-mode scanning performed by the convex probe according to a second ultrasonic imaging system.

In a second ultrasonic imaging system, a convex probe 10B is employed as shown in FIG. 11. It should be noted that since a hardware of this second ultrasonic imaging system except for the convex probe 10B is identical to that of the first ultrasonic imaging system, only structure/operation of this convex probe 10B are illustrated in FIG. 11. That is, in accordance with the second ultrasonic imaging system, the convex probe 10B having such a probe plane 30S that a plurality of transducer elements (not shown in detail) are arranged in an arc shape is driven by the pulser circuit 14 under control of the scanning controller 17 to scan the biological body 3 in the below-mentioned manner.

In FIG. 11, scanning lines B1, B2, - - - , Bn correspond to B-mode image scanning lines, whereas scanning lines B1′, B2′, - - - , Bn′ correspond to CFM-mode image scanning lines.

Figure 12:
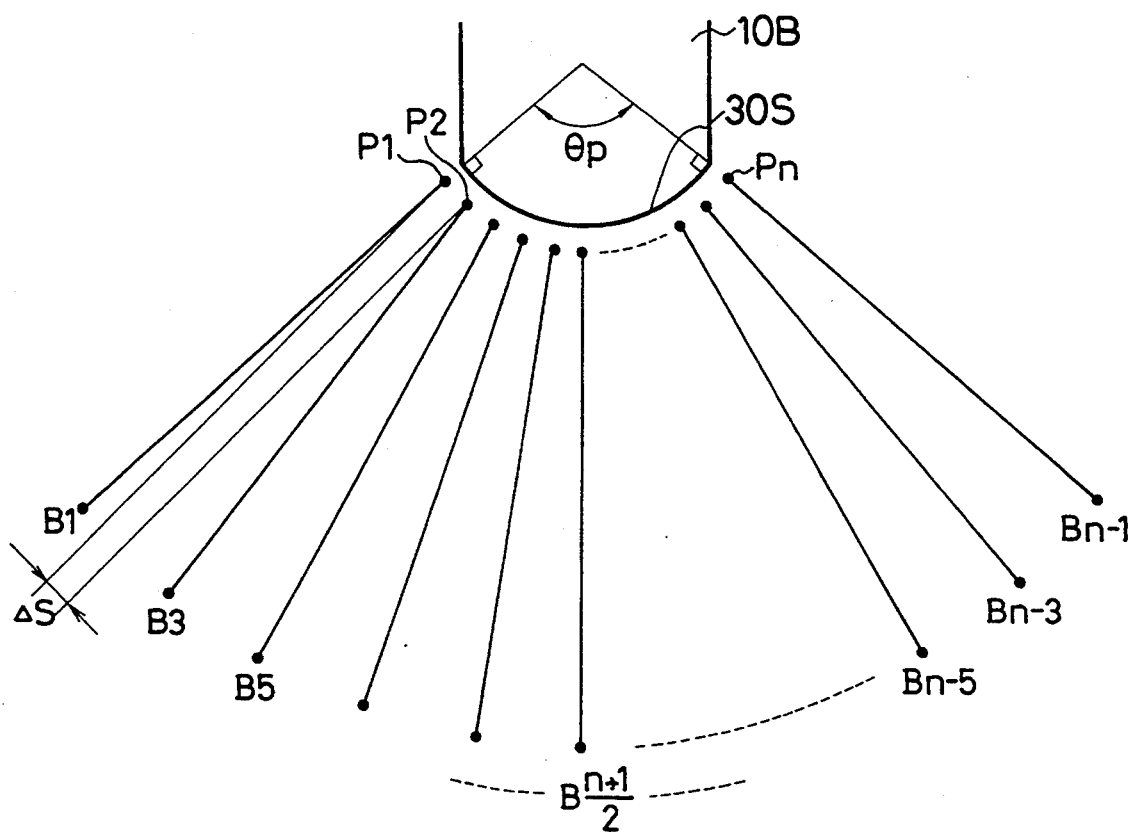
FIGS. 12 and 13 are enlarged illustrations of the fan-shaped B-mode/parallel CFM-mode scanning lines of the second ultrasonic imaging system.

FIG. 12 is an enlarged view of the B-mode image scanning lines B1, B2, - - - , Bn in which only odd-numbered scanning lines B1, B3, B5, - - - , Bn-1 are indicated. In FIG. 12, symbol "$\theta p$" indicates a projection angle of the probe plane 30S. Further, symbols P1, P2, - - - , Pn represent scanning start points for the B-mode scanning lines B1, B2, - - - , Bn, and for the CFM-mode scanning lines B1′, B2′, - - - , Bn′, and an interval "$\Delta S$" between the respective scanning start points P1, P2, - - - , Pn is defined by the following equation (4):

$$\Delta S = \frac{2\pi\theta}{360\,an}, \tag{4}$$

where symbol "$a$" indicates a curvature of the probe plane 30S of the convex probe 10B. At this time, a value of the scanning start point "Pk" is expressed by the following equation (5).

$$Pk = \Delta S \cdot k = \frac{2\pi\theta}{360\,an} \cdot k \tag{5}$$

It is assumed that coordinate of the scanning start point "p1" is 0.

As seen from FIG. 12, since the convex probe 10B is employed in the second ultrasonic imaging system, the B-mode scanning lines B1, B2, - - - , Bn are projected from the respective scanning start points P1, P2, - - - , Pn at a right (90°) angle with respect to the probe plane 30S, so that a fan-shaped range can be scanned.

In accordance with a similar manner to the first ultrasonic imaging system shown in FIG. 4 to 6, the scanning start points P1, P2, - - - Pn and the scanning directions with respect to the respective B-mode image scanning lines B1, B2, - - - , Bn are calculated based on the above formulae (4) and (5), and then stored in the scanning start-point data memory 106 and the scanning direction data (delay data) memory 108 employed in the scanning controller 17 (see FIG. 8). Thereafter, these data about the scanning start points and the scanning directions are sequentially supplied to the reception delay circuit 15 and the transmission delay circuit 16. As a consequence, the biological object 3 is sequentially scanned by utilizing these B-mode scanning lines B1, B2, - - - , Bn.

Similarly, ultrasonic echo information acquired along these B-mode scanning lines B1, B2, - - - , Bn is detected in the detector circuit 20, and the detected echo data are supplied to the DSC circuit 23. This DSC circuit 23 acquires a fan-shaped B-mode image from the detected echo data, and then the resultant fan-shaped B-mode image data is stored therein.

After the above-described B-mode image scanning operation with the scanning lines B1, - - - , Bn has been completed, a color blood-flow (CFM) image scanning operation is commenced with employment of this convex probe 10B.

Figure 13:
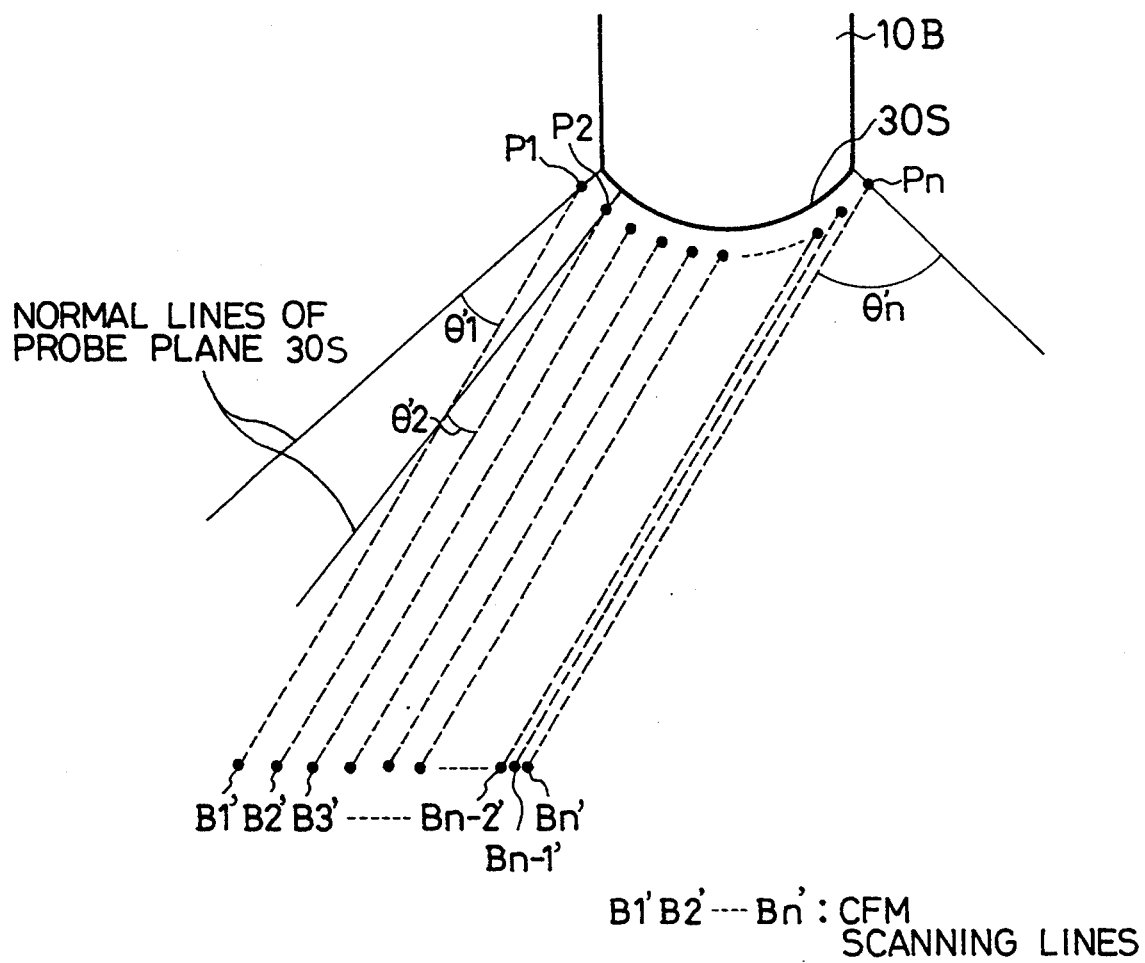

Referring now to an enlarged view of the CFM image scanning lines B1', B2' - - - , Bn' shown in FIG. 13, this CFM-mode scanning operation will be explained. In FIG. 13, symbols $\theta 1'$ $\theta 2'$, - - - , $\theta n'$ indicate angles (referred to "beam steering angles") between these CFM-mode scanning lines B1', B2', - - - , Bn' and the normal line directions of the probe plane 30S. As a major feature of the second ultrasonic imaging system, the CFM-image scanning lines B1', B2', - - - , Bn' are projected in parallel to each other, as illustrated in FIG. 13. To achieve such parallel CFM-image scanning beams, the above-described beam steering angle "$\theta k$" is defined as follows:

$$\theta k = \theta 1' - (k - 1) \cdot \frac{\theta}{n-1}. \quad (6)$$

The CFM-image scanning operation with employment of the convex probe 10B in accordance with the second ultrasonic imaging system is performed as follows.

In the scanning controller 17, both of scanning start-point data which have been already calculated for the B-mode image scanning lines B1, - - - , Bn, and scanning direction data ($\theta k$) are calculated with respect to the CFM-mode image scanning lines B1', - - - , Bn'. These data are sequentially supplied to the reception delay circuit 15 and the transmission delay circuit 16 in order to perform the CFM-mode image scanning operations with employment of the convex probe 10B.

Similarly, ultrasonic echo information acquired along the respective CFM-mode scanning lines B1', B2', - - - , Bn' is supplied to the CFM circuit 21 so as to calculated blood-flow velocities. The DSC circuit 23 produces a color blood-flow image where differences in these blood-flow velocities are represented as color differences, and also superimposes this color blood-flow image on the previously acquired B-mode image. As a result, a fan-shaped B-mode image is displayed with a color blood-flow image on the TV monitor 24 in such a manner that a portion of this fan-shaped B-mode image is superimposed on the color blood-flow image.

It should be noted that since the beam steering angle $\theta 1'$ may be changed by operating the operation panel 25, the actual display position of the color blood-flow image may be shifted along the horizontal directions, as viewed in FIG. 13.

THIRD ULTRASONIC IMAGING SYSTEM FOR TRANSMITTING SAME FAN-SHAPED B-MODE/CFM-MODE SCANNING BEAMS

Figure 14:
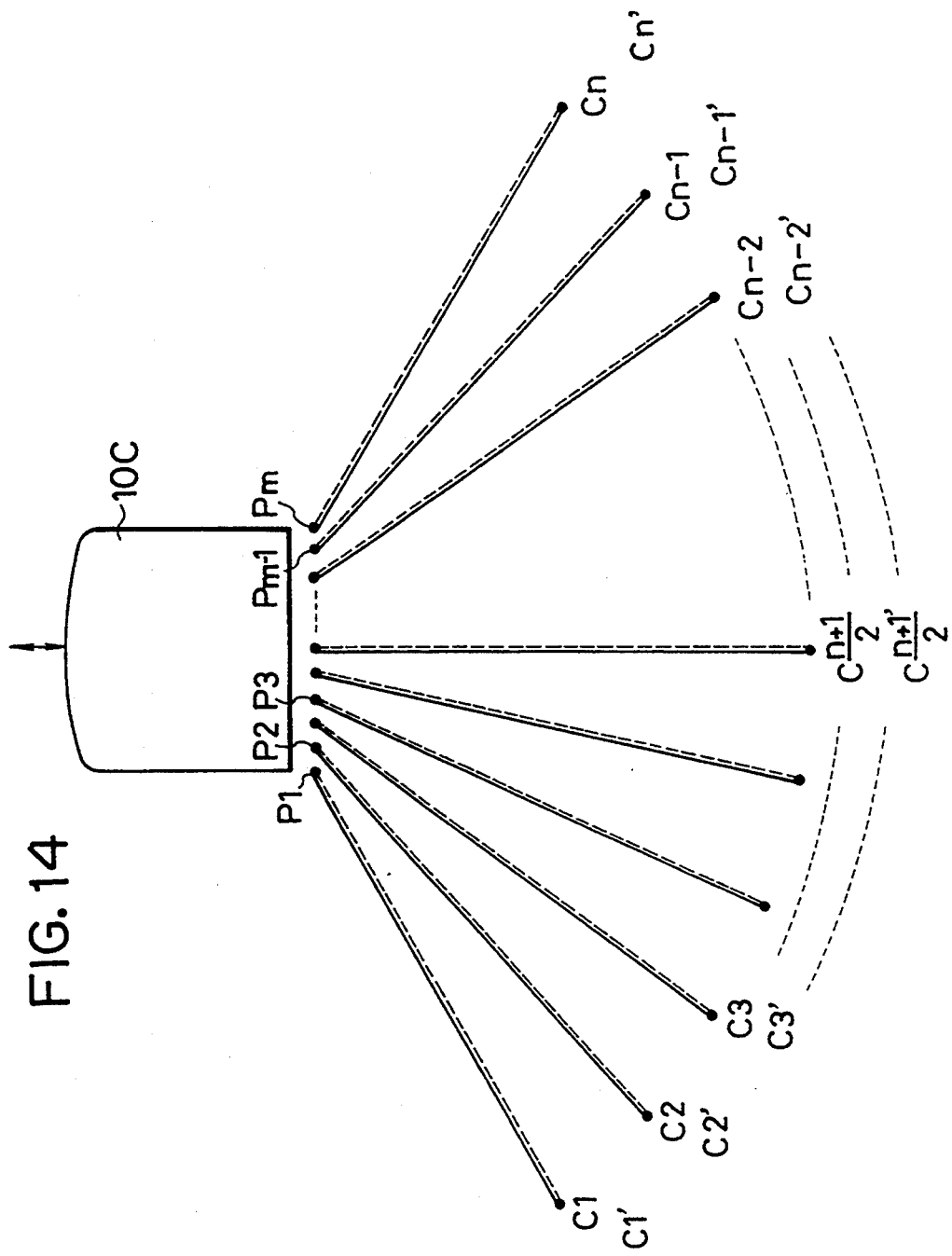
FIG. 14 schematically indicates fan-shaped B-mode/CFM-mode scanning lines according to a third ultrasonic imaging system.

FIG. 14 represents an ultrasonic imaging method according to a third preferred embodiment of the present invention, by which both of fan-shaped B-mode scanning beams and fan-shaped B-mode scanning beams are transmitted from a linear probe 10C. The shapes of these fans are substantially Identical to each other.

It should be noted that the structure of this linear probe 10C is the same as the above-described linear probe 10A employed in the first ultrasonic imaging system, but there is only difference between the probe driving methods thereof. That is, the calculations/determinations of the scanning start points/scanning directions for B-mode image scanning lines C1, C2, - - - , Cn are identical to those of the B-mode image scanning lines A1, A2, - - - , An in the first ultrasonic imaging system. In accordance with the third ultrasonic imaging system, these calculations/determinations for the B-mode image scanning lines C1, C2, - - - , Cn can be directly applied to those for CFM-mode image scanning lines C1', C2', - - - , Cn'.

It should also be noted that as described above, since these calculations/determinations of the scanning start points/scanning directions have be explained by using the equations (2) and (3) as to the first ultrasonic imaging system, no further explanation is made.

As readily seen from FIG. 14, a fan-shaped range can be scanned by both of the B-mode image scanning lines C1, C2, - - - , Cn, and the CFM-mode image scanning lines C1', C2', - - - , Cn', so that a fan-shaped color blood-flow image with a wider area than that of the previously explained color blood-flow images can be displayed on the TV monitor 24. Accordingly, since such a wide-ranged CFM image is displayed, abnormal blood flows appearing inside the biological body 3 can be easily diagnosed.

It should be understood that this linear probe 10C may be substituted by a convex probe (e.g., see FIG. 12).

FOURTH ULTRASONIC IMAGING SYSTEM FOR TRANSMITTING POSITIONALLY-SHIFTED FAN-SHAPED B-MODE/CFM-MODE SCANNING BEAMS

Figure 15:
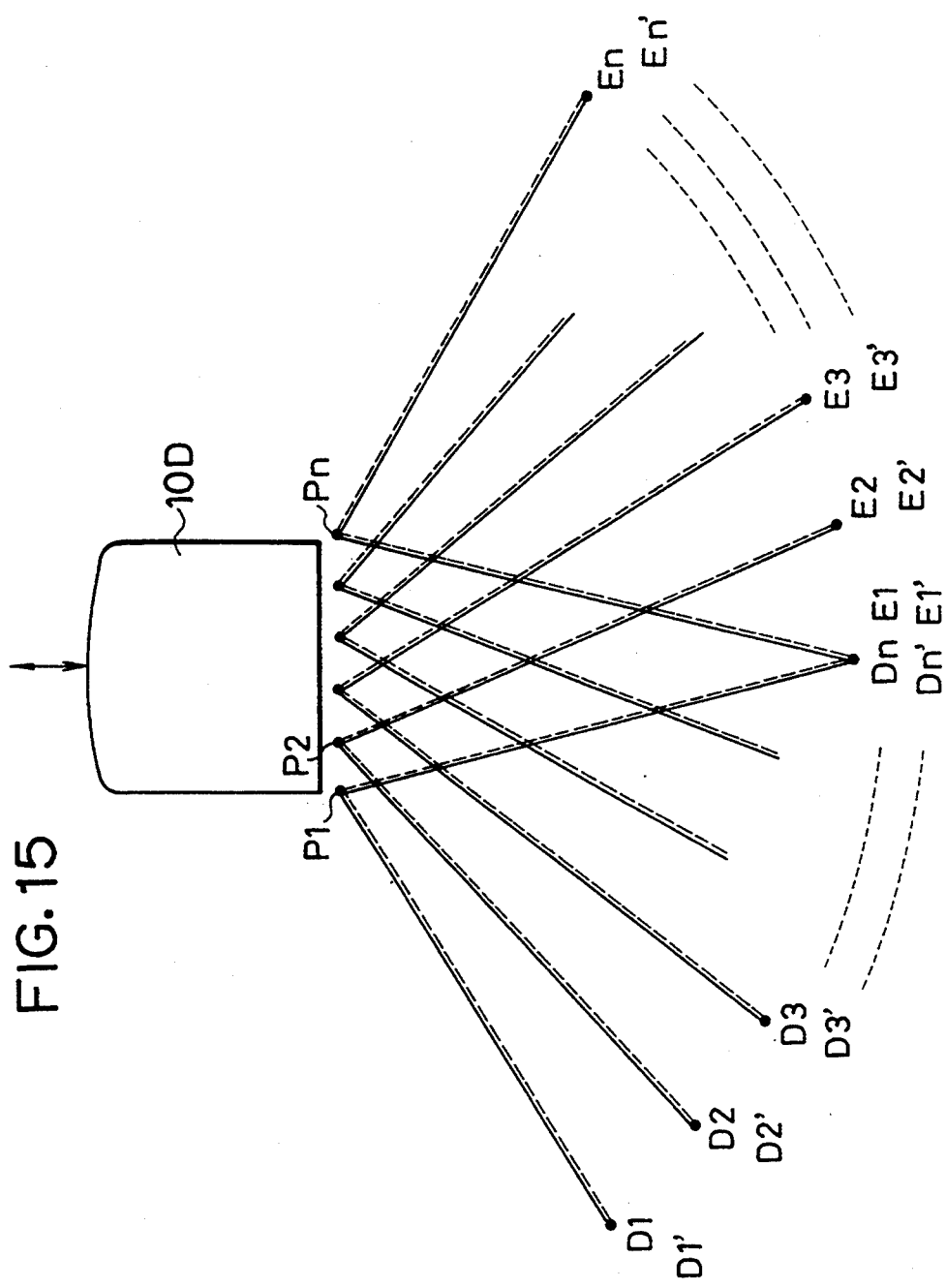
FIG. 15 schematically shows another fan-shaped B-mode/CFM-mode scanning form according to a fourth ultrasonic imaging system.

FIG. 15 represents an ultrasonic imaging method according to a fourth preferred embodiment of the present invention, by which two positionally-shifted fan-shaped ranges are scanned by B-mode image scanning beams and CFM-mode image scanning beams.

In this figure, scanning lines D1, D2, - - - , Dn and scanning lines E1, E2, - - - , En represent B-mode image scanning lines, whereas scanning lines D1', D2', - - - , Dn' and scanning lines E1', E2', - - - , En' denote CFM-mode image scanning lines.

As previously explained, the fan-shaped scanning range of the first ultrasonic scanning method is symmetric with respect to the right-hand range and the left-hard range (see FIG. 11). Thus, this fan-shaped scanning range may be positionally shifted along the right or left direction by adding a coefficient "$\theta a$" to the right term of the formula (2).

In accordance with the fourth ultrasonic imaging system, the ultrasonic imaging beams are transmitted along the above-described scanning lines D1, D2, - - - , Dn, E1, E2, - - - , En so as to obtain such a fan-shaped B-mode image. The scanning directions of these scanning lines D1, D2, ---, Dn, E1, E2, ---, En are calculated based upon the following equation (7):

$$\theta k = \theta 1 - (k - 1) \cdot \frac{2 \cdot \theta 1}{n - 1} + \theta a, \quad (7)$$

where for the scanning lines D1, D2, ---, Dn, $\theta a = +\theta 1$, and for the scanning lines E1, E2, ---, En, $\theta a = +\theta 1$.

Similarly, the scanning controller 17 calculates/stores the scanning start points P1, P2, ---, Pn and the scanning directions for the B-mode scanning lines D1, D2, ---, Dn and E1, E2, ---, En. These calculated data such as delay times are sequentially supplied to the reception delay circuit 15 and the transmission delay circuit 16. Accordingly, the fan-shaped range defined by the B-mode scanning lines D1 to En can be sequentially scanned to acquire fan-shaped B-mode image data by the DSC circuit 23.

After the above-described fan-shaped B-mode image scanning operation has been completed, a fan-shaped CFM-mode image scanning operation is commenced.

Since the scanning start-point data as well as the scanning direction data (i.e., delay time data) for the fan-shaped B-mode image scanning lines A1, ---, En are the same as those for these fan-shaped CFM-mode image scanning lines A1', ---, En', the scanning controller 17 sequentially supplies these data to the reception delay circuit 15 and the transmission delay circuit 16. As a result the fan-shaped region defined by these CFM-mode image scanning lines D1', ---, En' can be sequentially scanned to obtain blood-flow velocities in the CFM circuit 21. Thereafter, a fan-shaped color blood-flow image representative of differences in these blood-flow velocities as different colors can be displayed on the TV monitor 24 together with the above-described fan-shaped B-mode image in a superimpose form.

The fourth ultrasonic image scanning system has such a merit that since the scanning directions of the CFM-mode scanning lines located near the center portion of this fan-shaped scanning range are not coincident with the normal lines of the probe plane of this linear probe 10D, the blood-flow velocities near the center portion can be measured, as compared with that of the third ultrasonic image scanning system shown in FIG. 14. As a consequence, an overall area of this fan-shaped scanning range can be displayed as the color blood-flow image.

FIFTH ULTRASONIC IMAGING SYSTEM CAPABLE OF PARTIALLY DISPLAYING FAN-SHAPED CFM IMAGE

Figure 16:
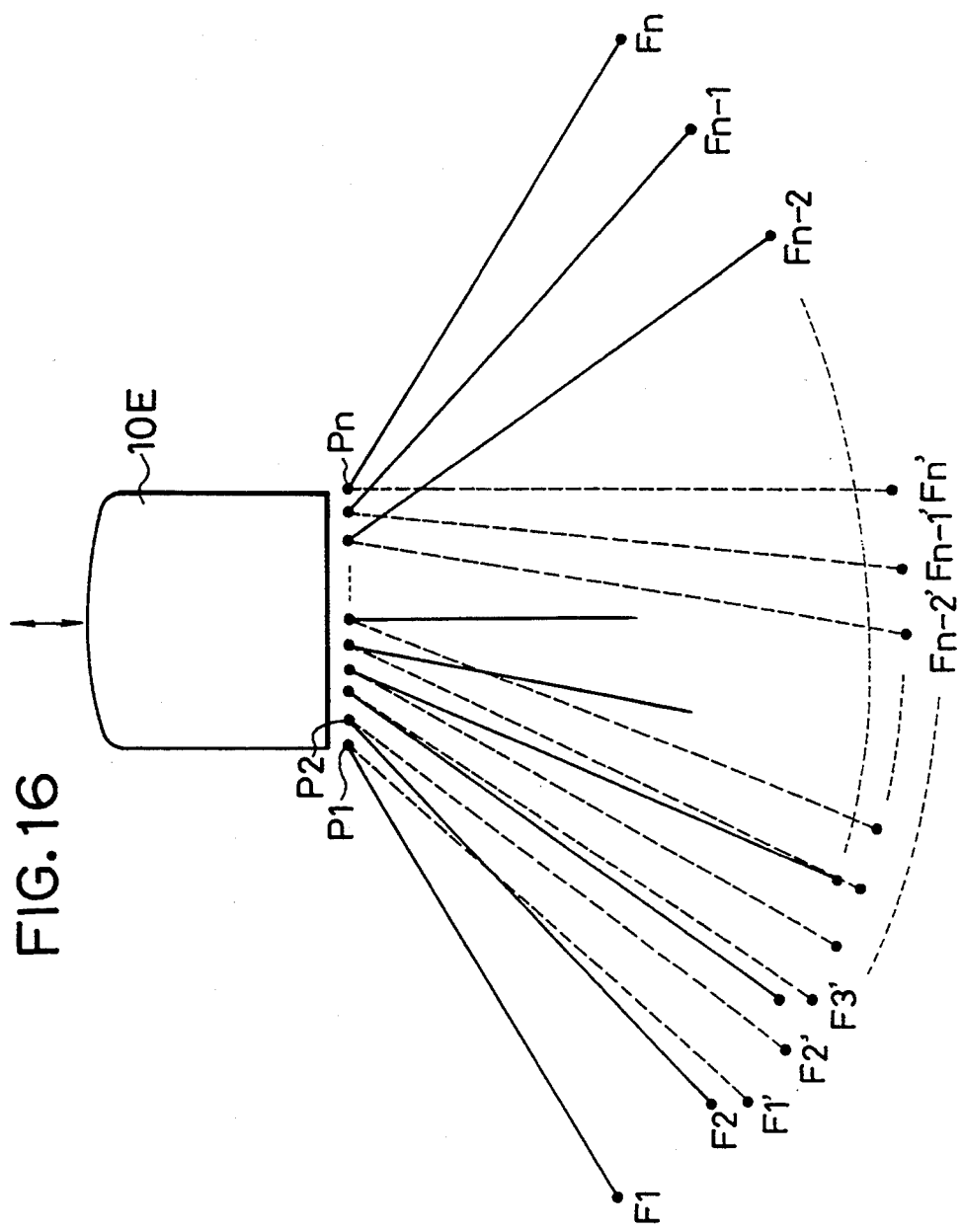
FIG. 16 schematically indicates another fan-shaped B-mode/CFM-mode scanning form according to a fifth ultrasonic imaging system.

As illustrated in FIG. 16, according to a fifth ultrasonic imaging system, a fan-shaped CFM-mode image is partially displayed on a fan-shaped B-mode image. A fan-shaped area of this CFM-mode image is smaller than that of the B-mode image.

In FIG. 16, scanning lines F1, F2, ---, Fn corresponds to the fan-shaped B-mode image scanning lines, and scanning lines F1', F2', ---, Fn' corresponds to the fan-shaped CFM-mode image scanning lines. A linear probe 10E is employed to transmit ultrasonic scanning beams along these scanning lines F1, ---, Fn, F1', ---, Fn'.

It should be noted that since these B-mode image scanning lines F1, F2, ---, Fn are similar to the B-mode image scanning lines A1, A2, ---, An of the first ultrasonic imaging system, both of scanning start-point data and scanning direction (delay time) data for this B-mode image scanning lines F1, F2, ---, Fn are calculated based on the above-explained formulae (2) and (3).

On the other hand, as previously explained, a fan-shaped range having an arbitrary dimension and an arbitrary direction can be scanned by transmitting the ultrasonic scanning beams along these CFM-mode image scanning lines F1', F2', ---, Fn'. The dimension and scanning direction of the CFM-ode image scanning lines F1', F2', ---, Fn' may be freely selected by changing the beam steering angles "$\theta 1$" and "$\theta a$" as defined in the above-described equation (7). Namely, $$\theta k = \theta 1 - (k - 1) \cdot \frac{2 \cdot \theta 1}{n - 1} + \theta a,$$

where the beam steering angles $\theta 1$ and $\theta a$ are variable. These beam steering angles are changeable by operating the operation panel 25.

In general, it is known that if a display range of a color blood-flow image would be excessively extended, resolution would be lowered. Under such circumstances, since only an arbitrary CFM-image range is displayed in the fifth ultrasonic imaging system, deterioration of resolution in a diagnostic range can be avoided.

SIXTH ULTRASONIC IMAGING SYSTEM WITH TRAPEZOID SCANNING

Figure 17:
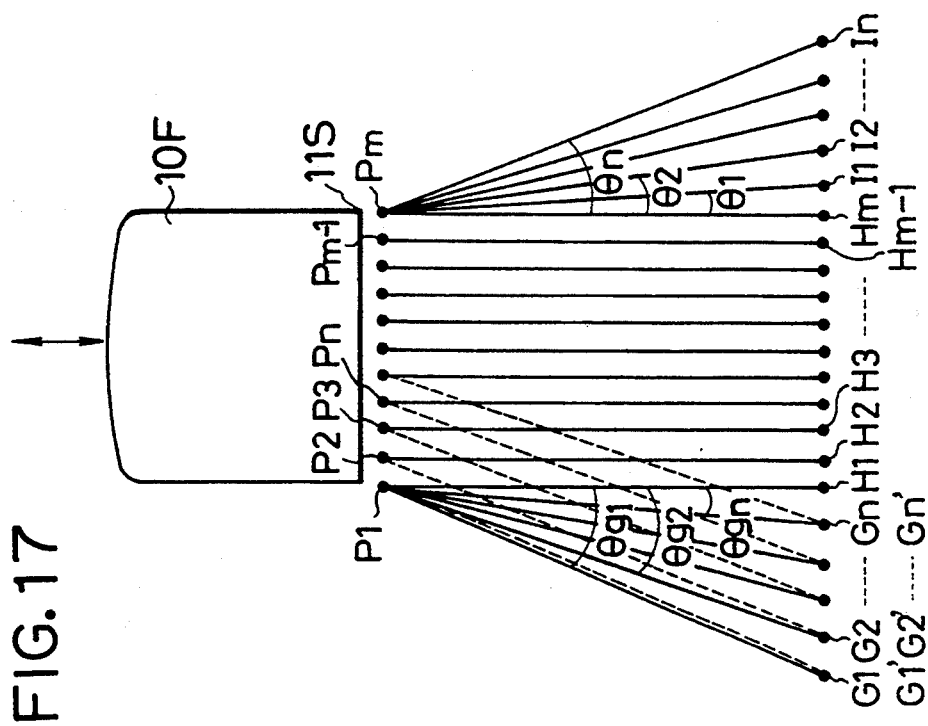
FIG. 17 schematically represents the trapezoid B-mode and the parallel CFM-mode scanning form according to sixth ultrasonic imaging system.

FIG. 17 shows a sixth ultrasonic imaging method with employment of a trapezoid scanning operation.

In FIG. 17, symbols P1, P2, ---, Pm indicates scanning start points of B-mode image scanning lines G1, ---, Gn, H1, ---, Hn, I1, ---, In ("m" being an integer larger than "n"). An interval of the successive scanning start points P1, ---, Pm is defined as S/m. Angles $\theta g1$, $\theta g2$, ---, $\theta gn$ denote an angle between each of the scanning lines G1, G2, ---, Gn and the normal line of the probe plane 11S of the linear probe 10F, namely, a beam steering angle, whereas angles $\theta i1$, $\theta i2$, ---, $\theta in$ indicate an angle between each of the scanning lines I1, I2, ---, In and the normal line of this probe plane 11S.

A scanning start point for all of the B-mode image scanning lines G1, G2, ---, Gn is indicated as "P1", and scanning directions of these scanning lines G1, ---, Gn are expressed by the following equation (8):

$$\theta gk = \theta g1 - (k - 1) \cdot \frac{2 \cdot \theta g1}{n}. \quad (8)$$

Figure 7:
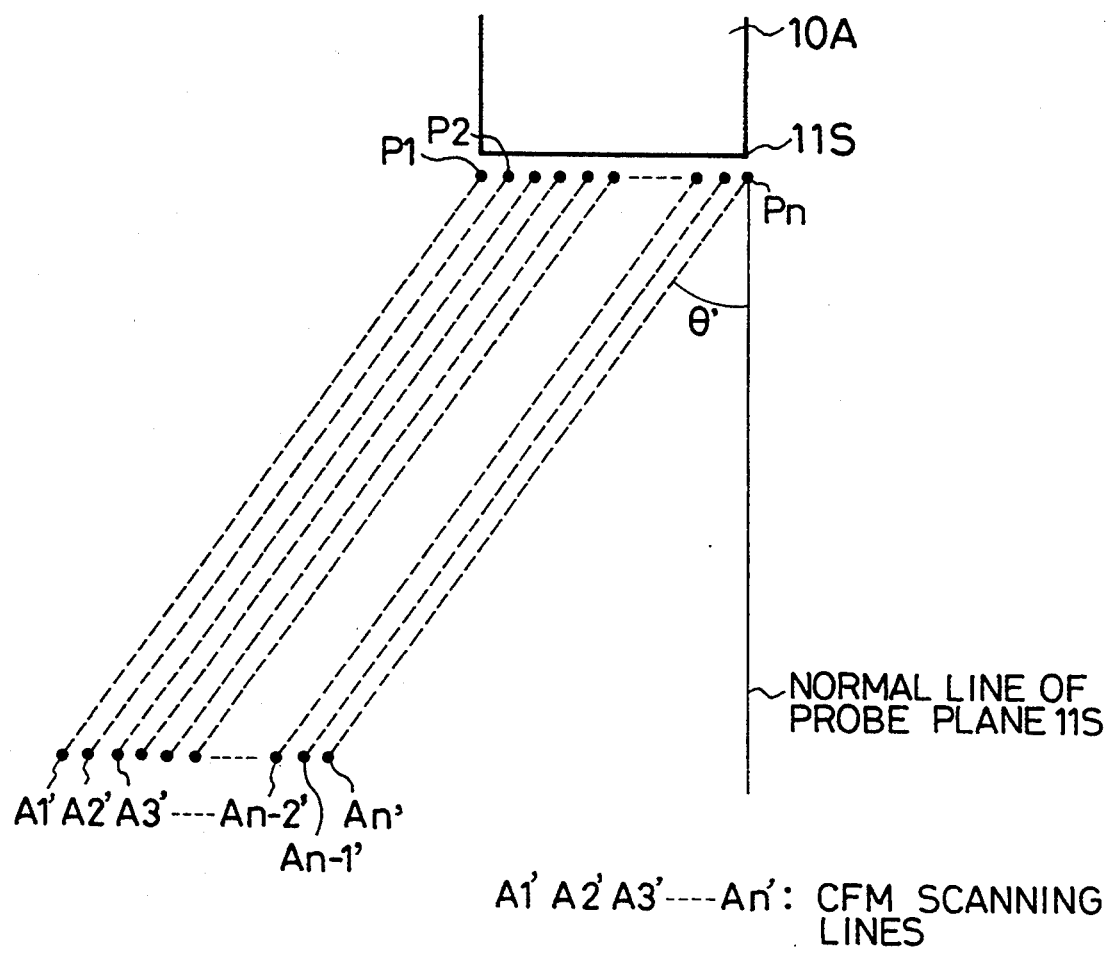
FIG. 7 is an enlarged illustration of the CFM scanning lines employed in the first ultrasonic imaging system.

Similarly, scanning start points for all of the CFM-mode image scanning lines G1', G2', ---, Gn' are the same as the above start point "p" for the B-mode image scanning lines A1, A2, ---, An (see FIG. 7). The scanning directions of these CFM-mode image scanning lines G1', G2', ---, Gn' can be calculated based on the above equation (2).

On the other hand, a scanning start point for all of the B-mode image scanning lines I1, I2, ---, In is indicated as "Pm", and scanning directions thereof are expressed by the following equation (9):

$$\theta ik = -(k - 1) \cdot \frac{2 \cdot \theta g1}{n}. \quad (9)$$

Furthermore, scanning start points for the B-mode scanning lines H1, H2, ---, Hm are indicated by P1, P2, ---, Pm, and scanning directions thereof are coincident with the normal lines of the probe plane 11S.

For the B-mode image scanning operation, the ultrasonic scanning beams are sequentially transmitted along all of the B-mode image scanning lines G1, - - -, Gn, H1, - - -, Hm, I1, - - -, In. Also, for the CFM-mode image scanning operation, the ultrasonic scanning beams are sequentially transmitted along only the CFM-mode image scanning lines G1', G2', - - -, Gn' and I1', I2', - - -, In'. Accordingly, the trapezoid B-mode scanning image together with the small CFM-mode scanning image made by only these parallel CFM-mode scanning lines G1', G2', - - -, Gn' can be displayed on the TV monitor 24 in a superimpose mode.

ANGLE CORRECTING CIRCUIT 22 FOR FAN-SHAPED CFM-MODE IMAGE SCANNING

As previously described, for instance, the first ultrasonic imaging system shown in FIG. 4 employs the angle correcting circuit 22. The function and an internal circuit arrangement of this angle correction circuit 22 will now be described in detail.

First, the reason why such an angle correction is required for a CFM-mode image scanning operation, will now be explained with reference to fan-shaped CFM-mode scanning beams represented in FIG. 18 (i.e., corresponding to the fan-shaped CFM-mode scanning beams of FIG. 14).

Figure 18:
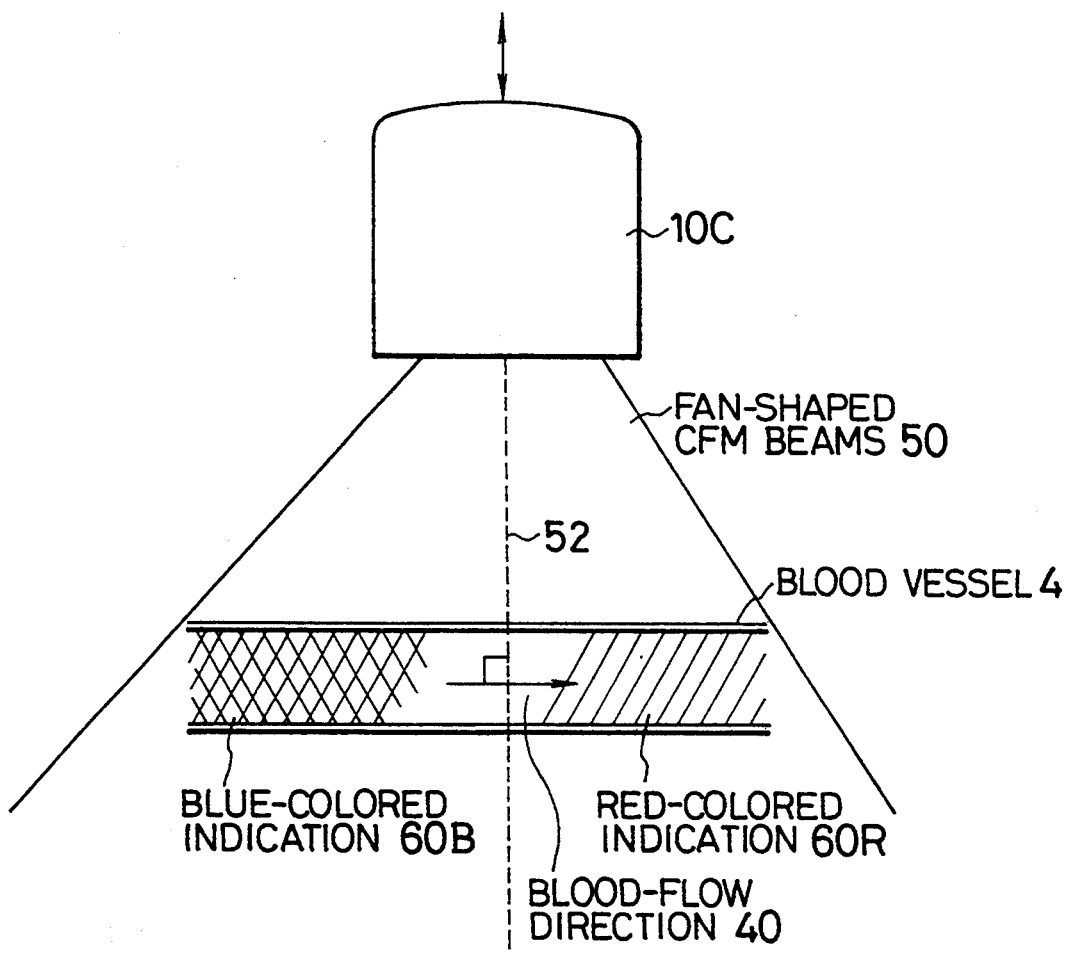
FIGS. 18 and 19 illustratively explain the angle correcting idea according to one of the major features of the present invention.

In FIG. 18, it is now assumed that fan-shaped CFM-mode scanning beams 50 are transmitted from the linear probe 10C to the blood vessel 4, through which blood is flown along the same blood-flow direction 40. When this blood-flow direction 40 intersects with the center beam 52 at a right angle, the velocity of the blood flow for the right side with respect to this center beam 52 is displayed in red (namely, red-colored indication 60R), whereas the velocity of the blood flow for the left side with respect to this center beam 52 is displayed in blue (namely, blue-colored indication 60B). Furthermore, color gradation for the same colored indication 60R, or 60B is changed. This is caused by the below-mentioned reason:

That is to say, since the angle "$\theta$" of $\cos\theta$ in the shift frequency "$f\alpha$" indicated in the above-described equation (1) corresponds to an incident angle of the fan-shaped ultrasonic beam 50, the sign thereof is inverted at the boundary position (namely, center beam 52). Furthermore, even in the same sign, since the blood-flow value "$f\alpha$" is varied, such a color inversion occurs even in the same blood-flow direction.

Accordingly, according to another feature of the present invention, the incident angles "$\theta$" of the ultrasonic beams (i.e., fan-shaped CFM-mode scanning beams 50) are corrected by proper correction values with regard to the respective ultrasonic beams. As a result, a blood flow along the same direction at the same velocity can be displayed in a monocolor.

The above-described angle correcting idea of the present invention will now be explained by way of a mathematical method with reference to FIG. 19.

Figure 19:
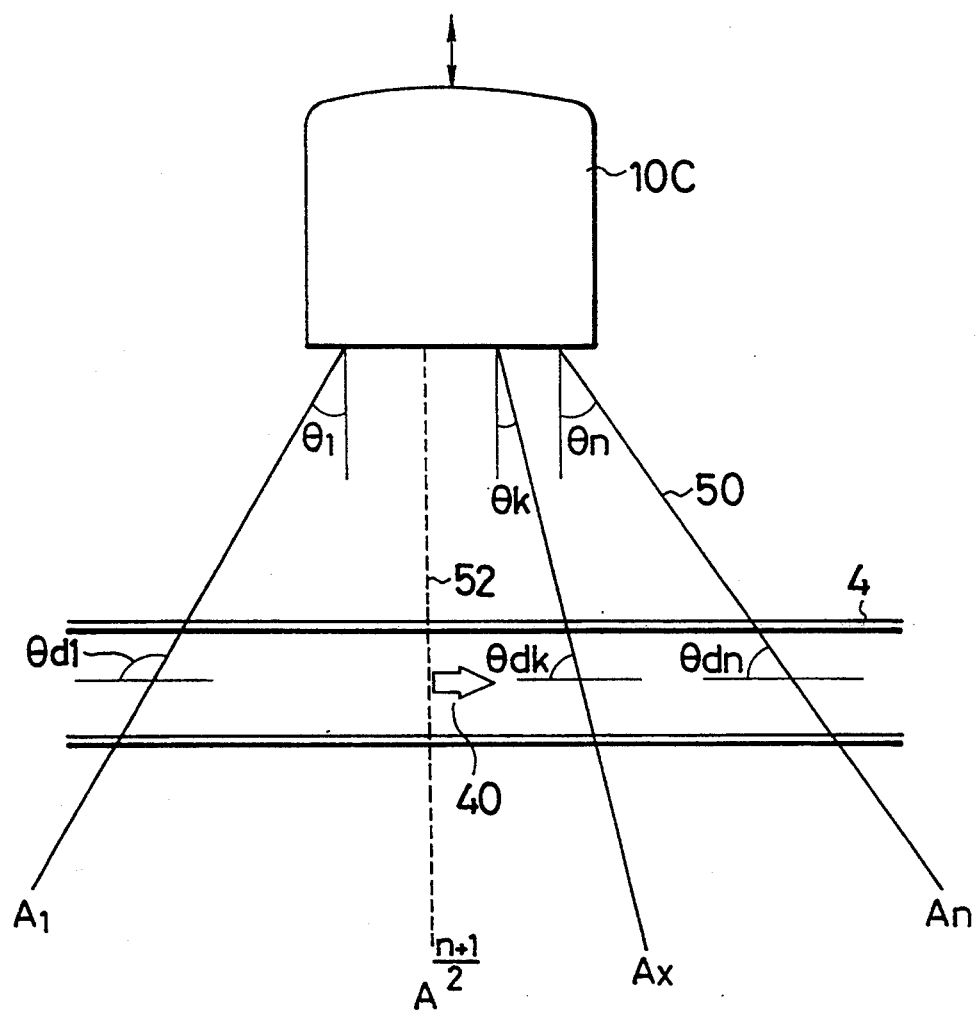

In FIG. 19, it is assumed that a blood flow along the right direction is displayed in red, whereas a blood flow along the left direction is displayed in blue.

The beam steering angle "$\theta k$" is defined in the equation (2), i.e., $$\theta k = \theta 1 - (k - 1) \cdot \frac{2 \cdot \theta 1}{n - 1}$$

Another angle "$\theta dk$" intersecting between the fan-shaped CFM-mode scanning beam 50 and the blood flow 40 is defined by:

$$\theta dk = 90° + \theta k \qquad (10).$$

Furthermore, an angle between this scanning beam 50 and the blood flow 40 is not equal to 90° at $A^{(n+1)/2}$ (namely, center beam 52), but is equal to 90° at $A_x$. That is, this condition is satisfied when the blood vessel 4 is inclined with respect to that of FIG. 19. In this inclined vessel condition, the angle correcting formula $\theta dk$ is given as follows:

$$\theta dk = 90° + \theta k + \theta x \qquad (11).$$

Accordingly, the sign of this beam steering angle $\theta k$ is defined as follows (see formula 2). If $k > A^{(n+1)/2}$, then the sign of the beam steering angle $\theta k$ becomes (—: negative). If $k \leq A^{(n+1)/2}$, then the sign of the beam steering angle $\theta k$ becomes (+: positive).

The position of this scanning beam $A_x$ is set by the operation panel 25 to determine which number of the raster (x). Then, the angle $\theta x$ corresponding to this raster number (x) is calculated, and $\theta x$ is added to all rasters. This angle $\theta x$ corresponds to the above-described angle correction value.

Figure 20:
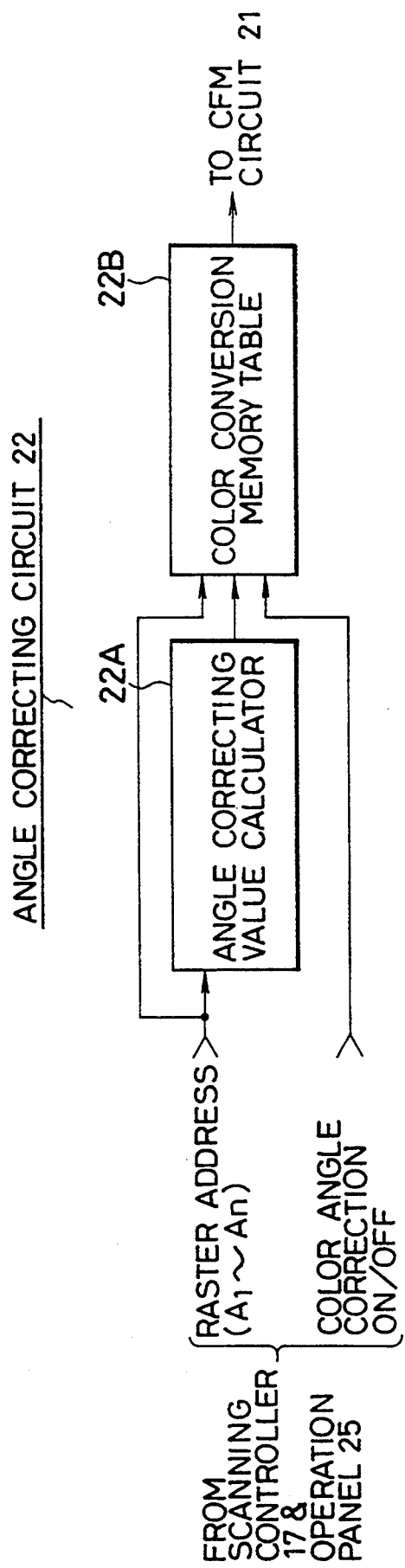
FIG. 20 schematically shows an internal circuit arrangement of the angle correcting circuit 22 indicated in FIG. 14.

FIG. 20 shows an internal circuit arrangement of this angle correcting circuit 22. This angle correcting circuit 22 is constructed of an angle correcting value calculator 22A for calculating the above-described formulae (10) and (11), and a color conversion memory table 22B. The color conversion memory table 22B stores table data for converting colors for the respective angles 0° to 360°, so that coloring operations corresponding to the respective angles intersecting between the respective fan-shaped CFM-mode scanning beams 50 and the blood flow 40 can be achieved.

Furthermore, the operation panel 25 may send an instruction to turn ON/OFF the angle correcting operation by the angle correcting circuit 22.

Figure 21:
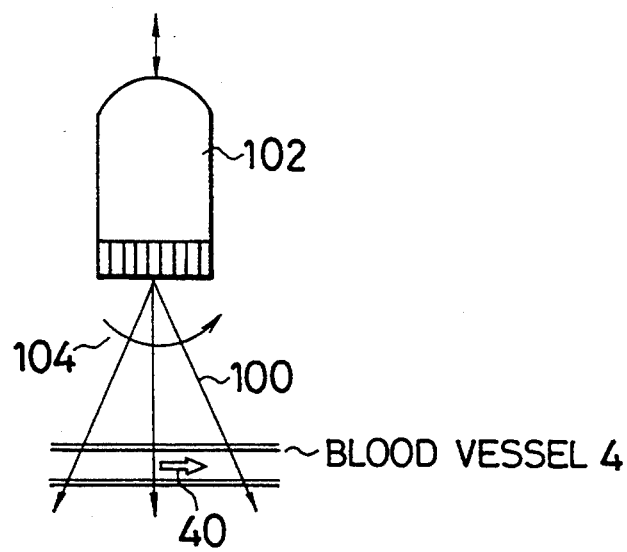
FIG. 21 is an illustration of the typical sector scanning mode required for the angle correcting operation of the present invention.
Figure 22:
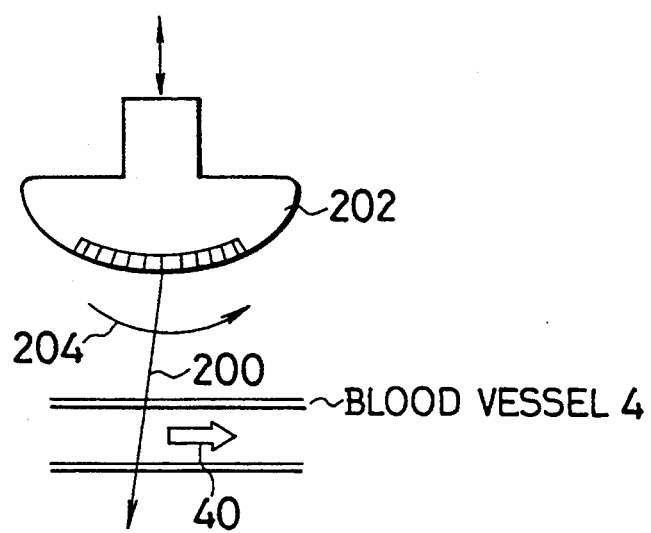
FIG. 22 is an illustration of the typical convex scanning mode required for the angle correcting operation of the present invention.

As previously explained, this angle correcting operation according to one of the major features of the present invention, is required not only for the above-described fan-shaped CFM-mode scanning beams 50 (see FIG. 18), but also for other fan-shaped beam cases. For instance, FIG. 21 represents the known sector scanning operation. In FIG. 21, since fan-shaped beams 100 used to the CFM-mode scanning operation is transmitted from the sector scanning probe 102 and scanned along a scanning direction 104, such an angle correcting operation may be utilized so as to display the blood flow 40 with the same direction in the same single color.

Figure 1:
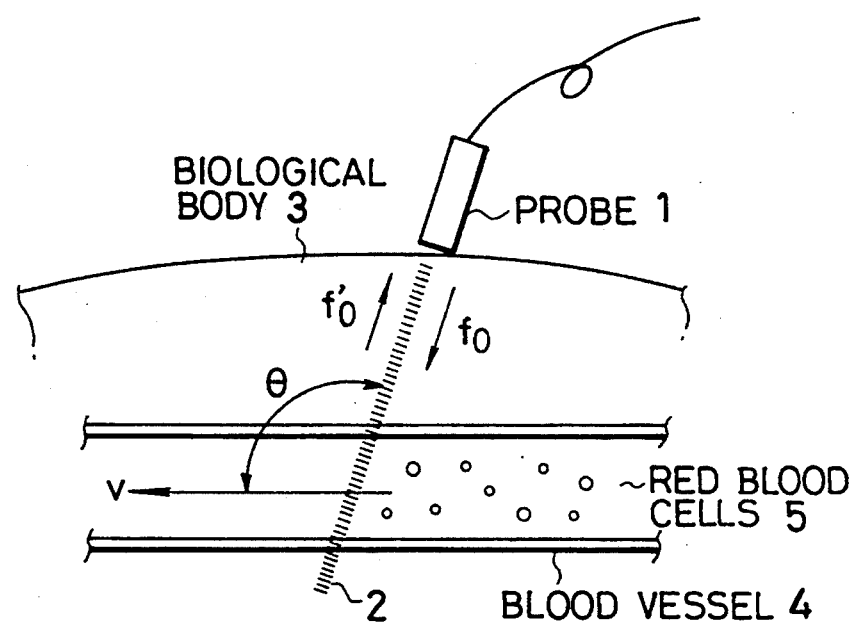
FIG. 1 schematically represents the basic blood-flow velocity measuring method by Doppler method.
Figure 2:
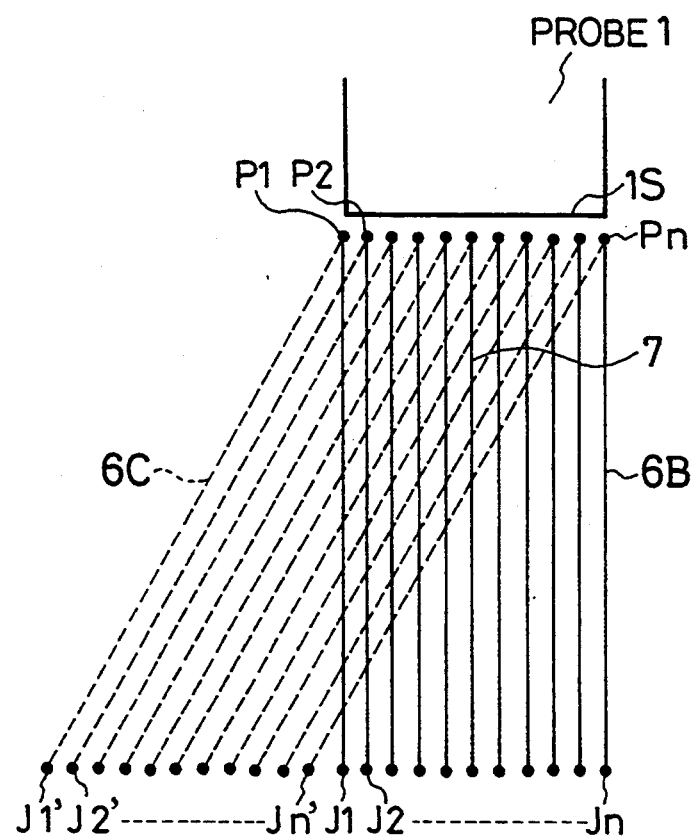
FIG. 2 schematically illustrates the first conventional linear scanning method with B-mode/CFM-mode.
Figure 3:
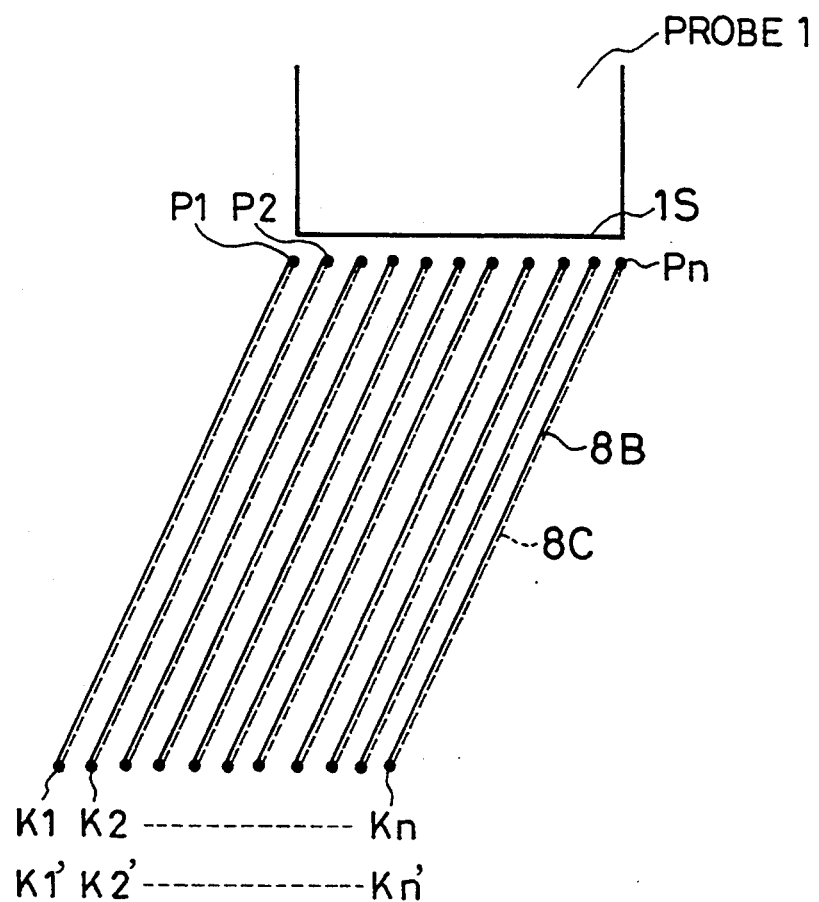
FIG. 3 schematically shows the second conventional linear scanning method with B-mode/CFM mode.

Similarly, FIG. 2 represents the known convex scanning operation. Since the ultrasonic beam 200 is transmitted from the convex scanning probe 202 and scanned, or steered along am arrow direction 204, the scanned shaped by the ultrasonic beam 200 constitutes a fan-shape. Accordingly, the above-explained angle correcting operation is similarly required.

As previously described in detail, according to the basic ideas, the present invention is not limited to the above-described preferred embodiments, but may be changed, modified and substituted without departing from the technical scope and spirit of the present invention.

For instance, when an ultrasonic diagnostic operation is actually performed, the above-described first to sixth scanning methods may be combined with each other in order to effectively perform this diagnostic operation. In one actual diagnostic operation, first, the fan-shaped color blood-flow image with the wider range is displayed as indicated in FIG. 14 (third scanning method) or FIG. 15 (fourth scanning method). As a result, abnormal blood flows can be easily found out and the actual position where such abnormal blood flows happen to occur, can be correctly recognized. Thereafter, another color blood-flow image with high resolution produced by the first, second, or third ultrasonic scanning method is displayed for the ultrasonic diagnostic operations.

What is claimed is:

1. An ultrasonic imaging system comprising:
    probe means having a probe plane for transmitting ultrasonic pulses to an interior portion of a biological body under medical examination, and for receiving ultrasonic echoes reflected from the interior portion of the biological body;
    B-mode image scanning means coupled to the probe means, for scanning said interior portion of the biological body by said ultrasonic pulses in a fan-shaped form as fan-shaped B-mode image scanning beams;
    B-mode image producing means for producing B-mode image data of said scanned interior portion from B-mode imaging echoes derived from said probe means, while scanning said interior portion by said fan-shaped B-mode image scanning beams;
    blood-flow image scanning means for scanning said interior portion, while transmitting thereto said ultrasonic pulses as blood-flow image scanning beams from said probe plane at a preselected inclined angle with respect to a normal line direction of said probe plane;
    blood-flow image producing means for producing blood-flow image data of said scanned interior portion from blood-flow imaging echoes derived from said probe means, while scanning said interior portion by said inclined blood-flow image scanning beams;
    correcting means for correcting a color indication of a blood-flow direction of blood, said color indication being varied in accordance with an incident angle of said blood-flow image scanning beams with respect to said blood-flow direction of the blood within a blood vessel, even when said blood is flown along the same direction; and
    dual-mode displaying means for displaying both of a B-mode image of said scanned interior portion and a blood-flow image thereof in a dual mode by superimposing said blood-flow image data on said B-mode image data.

2. An ultrasonic imaging system as claimed in claim 1, wherein said correcting means includes:
    an angle correcting value calculator for calculating an angle correcting value in accordance with each address data about said blood-flow image scanning beams; and
    a color conversion memory table for previously storing data used to convert one color into another color with respect to said incident angles of said blood-flow image scanning beams.

3. An ultrasonic imaging system as claimed in claim 1, wherein said blood-flow image scanning means and and B-mode image scanning means commonly includes at least scanning control means comprising:
    means for calculating scanning start-point data with respect to each of said fan-shaped B-mode image scanning beams and said inclined blood-flow image scanning beams; and
    means for calculating scanning direction data with respect to each of said fan-shaped B-mode image scanning beams and said inclined blood-flow image scanning beams, and for converting said scanning direction data into delay time data, said delay time data being supplied at least to said B-mode image scanning means and said blood-flow image scanning means, whereby said B-mode image scanning beams are transmitted in a predetermined fan-shape and said blood-flow image scanning beams are transmitted at a predetermined inclined angle with respect to the normal line direction of said probe plane.

4. An ultrasonic imaging system as claimed in claim 3, wherein said scanning control means further includes:
    means for controlling a beam steering angle of said blood-flow image scanning beams, whereby said blood-flow image scanning beams are transmitted at an arbitrary inclined angle with respect to the normal line direction of the probe plane.

5. An ultrasonic imaging system as claimed in claim 1, wherein said probe means is a linear scanning probe.

6. An ultrasonic imaging system as claimed in claim 1, wherein said probe means is a convex scanning probe.

7. An ultrasonic imaging system as claimed in claim 1, wherein said blood-flow image scanning means produces fan-shaped blood-flow image scanning beams to scan the interior portion of the biological body by said fan-shaped blood-flow image scanning beams.

8. An ultrasonic imaging method comprising the steps of:
    transmitting ultrasonic pulses from a probe plane of an ultrasonic probe to an interior portion of a biological body under medical examination;
    receiving ultrasonic echoes reflected from the interior portion of the biological body;
    scanning said interior portion of the biological body by said ultrasonic pulses in a fan-shaped form as fan-shaped B-mode image scanning beams;
    producing B-mode image data of said scanned interior portion from B-mode imaging echoes derived from said probe, while scanning said interior portion by said fan-shaped B-mode image scanning beams;
    scanning said interior portion, while transmitting thereto said ultrasonic pulses as blood-flow image scanning beams from said probe plane at a preselected inclined angle with respect to a normal line direction of said probe plane;
    producing blood-flow image data of said scanned interior portion from blood-flow imaging echoes derived from said probe, while scanning said interior portion by said inclined blood-flow image scanning beams;
    correcting a color indication of a blood-flow direction of blood, said color indication being varied in accordance with an incident angle of said blood-flow image scanning beams with respect to said blood-flow direction of the blood within a blood vessel, even when said blood is flown along the same direction; and
    displaying both of a B-mode image of said scanned interior portion and a blood-flow image thereof in a dual mode by superimposing said blood-flow image data on said B-mode image data.

9. An ultrasonic imaging method as claimed in claim 8, wherein said correcting step further includes the steps of:
- calculating an angle correcting value in accordance with each address data about said blood-flow image scanning beams; and
- previously storing data used to convert one color into another color with respect to said incident angles of said blood-flow image scanning beams.

10. An ultrasonic imaging method as claimed in claim 8, further comprising the step of:
- controlling a beam steering angle of said blood-flow image scanning beams with respect to said scanned interior portion, whereby said blood-flow image scanning beams are transmitted at an arbitrary inclined angle with respect to the normal line direction of the probe plane.

11. An ultrasonic imaging method as claimed in claim 8, further comprising the step of:
- controlling a beam steering angle of said blood-flow image scanning beams in such a manner that said blood-flow image scanning beams are transmitted in parallel to each other from the probe plane.

12. An ultrasonic imaging method as claimed in claim 8, further comprising the step of:
- controlling a beam steering angle of said blood-flow image scanning beams so as to scan the interior portion of the biological body by fan-shaped blood-flow image scanning beams.

13. An ultrasonic imaging method as claimed in claim 8, further comprising the step of:
- transmitting said B-mode image scanning beams in a trapezoid form and said blood-flow image scanning beams at a predetermined inclined angle with respect to the probe plane thereof.

* * * * *